(12) United States Patent
Blume et al.

(10) Patent No.: US 10,704,037 B2
(45) Date of Patent: Jul. 7, 2020

(54) PROCESSES FOR THE MANUFACTURE AND USE OF PANCREATIN

(71) Applicant: Abbott Products GmbH, Hanover (DE)

(72) Inventors: Heinz Blume, Neustadt (DE); Martin Frink, Wedemark (DE); Claus-Juergen Koelln, Neustadt (DE); Michael Rust, Sehnde (DE)

( * ) Notice: Subject to any disclaimer, the term of this patent is extended or adjusted under 35 U.S.C. 154(b) by 0 days.

(21) Appl. No.: 15/214,973

(22) Filed: Jul. 20, 2016

(65) Prior Publication Data
US 2017/0073660 A1 Mar. 16, 2017

Related U.S. Application Data

(63) Continuation of application No. 11/460,330, filed on Jul. 27, 2006, now abandoned.

(60) Provisional application No. 60/703,813, filed on Jul. 29, 2005.

(51) Int. Cl.
*C12N 9/94* (2006.01)
*A61K 38/00* (2006.01)

(52) U.S. Cl.
CPC ............... *C12N 9/94* (2013.01); *A61K 38/00* (2013.01)

(58) Field of Classification Search
CPC .......... A61K 38/00; C12N 9/94; C03C 15/00; G02B 5/0268; G02B 6/0043; G02B 6/0061; G02B 6/0065
See application file for complete search history.

(56) References Cited

U.S. PATENT DOCUMENTS

| | | | |
|---|---|---|---|
| 2,189,948 A | 2/1940 | Griffith et al. | |
| 2,503,313 A | 4/1950 | Levin | |
| 3,324,002 A | 6/1967 | Antonides | |
| 3,803,305 A | 4/1974 | Thuillier | |
| 3,950,508 A | 4/1976 | Mony et al. | |
| 3,956,483 A | 5/1976 | Lewis | |
| 3,986,927 A | 10/1976 | Melnick et al. | |
| 3,991,180 A | 11/1976 | Boettner et al. | |
| 4,019,958 A | 4/1977 | Hell et al. | |
| 4,079,125 A | 3/1978 | Sipos | |
| 4,106,991 A | 8/1978 | Markussen et al. | |
| 4,242,219 A | 12/1980 | Bogerman et al. | |
| 4,280,971 A | 7/1981 | Wischniewski et al. | |
| 4,447,412 A | 5/1984 | Bilton | |
| 4,456,590 A * | 6/1984 | Rubinstein | A61L 2/0023 514/13.7 |
| 4,490,361 A | 12/1984 | Heldebrant | |
| 4,495,278 A | 1/1985 | Thomas | |
| 4,533,562 A | 8/1985 | Ikagami et al. | |
| 4,623,624 A | 11/1986 | Schullze | |
| 4,689,297 A | 8/1987 | Good et al. | |
| 4,775,536 A | 10/1988 | Patell | |
| 4,786,505 A | 11/1988 | Lovgren et al. | |
| 4,929,774 A | 5/1990 | Fukamachi et al. | |
| 5,068,110 A | 11/1991 | Fawzi et al. | |
| 5,219,572 A | 6/1993 | Sivaramakrishman et al. | |
| 5,225,202 A | 7/1993 | Hodges et al. | |
| 5,260,074 A | 11/1993 | Sipos | |
| 5,300,433 A | 4/1994 | Hrinda et al. | |
| 5,302,400 A | 4/1994 | Sipos | |
| 5,324,649 A | 6/1994 | Arnold et al. | |
| 5,374,657 A | 12/1994 | Kyle | |
| 5,378,462 A | 1/1995 | Boedecker et al. | |
| 5,489,530 A | 2/1996 | Braatz et al. | |
| 5,536,661 A | 7/1996 | Boel et al. | |
| 5,570,104 A | 10/1996 | Hayashi | |
| 5,614,189 A | 3/1997 | Huge-Jensen | |
| 5,618,710 A | 4/1997 | Navia et al. | |
| 5,645,832 A | 7/1997 | Braatz et al. | |
| 5,658,871 A | 8/1997 | Batenburg et al. | |
| 5,719,115 A | 2/1998 | Paatz et al. | |
| 5,725,880 A | 3/1998 | Hirakawa et al. | |
| 5,750,104 A | 5/1998 | Sipos | |
| 5,750,148 A | 5/1998 | Maruyama et al. | |
| 5,766,912 A | 6/1998 | Boel et al. | |
| 5,783,545 A | 7/1998 | Paatz et al. | |
| 5,801,022 A | 9/1998 | Navia et al. | |
| 5,849,296 A | 12/1998 | Navia et al. | |
| 5,863,759 A | 1/1999 | Boel et al. | |
| 5,869,438 A | 2/1999 | Svendsen et al. | |
| 5,874,558 A | 2/1999 | Boel et al. | |
| 6,004,768 A | 2/1999 | Navia et al. | |
| 5,879,920 A | 3/1999 | Dale et al. | |
| 5,976,529 A | 11/1999 | Navia et al. | |

(Continued)

FOREIGN PATENT DOCUMENTS

| | | |
|---|---|---|
| CA | 2263703 | 8/1999 |
| DE | 2035739 A1 | 1/1972 |

(Continued)

OTHER PUBLICATIONS

Miwa et al. (nt. J. Pharmaceutics (2000) 195: 81-92 (Year: 2000).*
Zaks et al. Science, New Series (1984) 224(4654): 1249-1251 (Year: 1984).*
"Gastric juice" (http://www.thefreedictionary.comIgastric+juice) accessed Aug. 2, 2013.
"Pancreatin juice", The American Heritage Dictionary of the English Language, 4th Edition Boston, Houghton Mifflin (2002). www.bartleby.com/61/ (printed Mar. 21, 2007).
"Pancreatin", The American Heritage Dictionary of the English Language, 4th Edition Boston, Houghton Mifflin (2002). www.bartleby.com/61/ (printed Mar. 21, 2007).
16 Overland, et al., "Lecithin in Swine Diets: I. Weanling Pigs," J. Anim Sci, 71:1187-1193 (1993).

(Continued)

*Primary Examiner* — Susan M Hanley
(74) *Attorney, Agent, or Firm* — Neal, Gerber & Eisenberg LLP

(57) ABSTRACT

A process for the manufacture and use of pancreatin in which the concentration of one or more biological contaminants is reduced, such as viruses and/or bacteria, through heating the pancreatin at a temperature of at least 85° C. for a period of less than about 48 hours.

22 Claims, 5 Drawing Sheets

(56) References Cited

U.S. PATENT DOCUMENTS

| | | |
|---|---|---|
| 5,993,806 A | 11/1999 | Galle |
| 6,011,001 A | 1/2000 | Navia et al. |
| 6,025,391 A | 2/2000 | Haeberlin et al. |
| 6,030,798 A | 2/2000 | Braatz et al. |
| 6,051,220 A | 4/2000 | Scharpe |
| 6,054,136 A | 4/2000 | Farah et al. |
| 6,140,475 A | 10/2000 | Margolin et al. |
| 6,187,572 B1 | 2/2001 | Platz et al. |
| 6,224,910 B1 | 5/2001 | Ullah et al. |
| 6,267,985 B1 | 7/2001 | Chen et al. |
| 6,278,794 B1 | 8/2001 | Parekh et al. |
| 6,312,704 B1 | 11/2001 | Farah et al. |
| 6,348,442 B2 | 2/2002 | Markussen |
| 6,355,461 B2 | 3/2002 | Henriksen et al. |
| 6,426,091 B1 | 7/2002 | Okumura et al. |
| 6,692,771 B2 | 2/2004 | Pather et al. |
| 6,734,188 B1 | 5/2004 | Rhodes et al. |
| 6,749,851 B2 | 6/2004 | Mann et al. |
| 6,767,729 B1 | 7/2004 | Nagano et al. |
| 6,783,968 B2 * | 8/2004 | Drohan .................. C12N 13/00 424/94.3 |
| 7,211,281 B2 | 5/2007 | Van Beek et al. |
| 7,479,378 B2 | 1/2009 | Potthoff et al. |
| 7,658,918 B1 | 2/2010 | Ortenzi |
| 8,221,747 B2 | 7/2012 | Ortenzi |
| 8,246,950 B2 | 8/2012 | Ortenzi |
| 2001/0046493 A1 | 11/2001 | Margolin et al. |
| 2002/0061302 A1 | 5/2002 | Sander-Struckmeier et al. |
| 2002/0076438 A1 | 6/2002 | Ullah et al. |
| 2002/0137156 A1 | 9/2002 | Margolin et al. |
| 2002/0146451 A1 | 10/2002 | Sharma et al. |
| 2003/0007962 A1 | 1/2003 | Vergez et al. |
| 2003/0017144 A1* | 1/2003 | Margolin ............... A61K 38/47 424/94.2 |
| 2003/0021844 A1 | 1/2003 | Barthelemy et al. |
| 2003/0049245 A1 | 3/2003 | Mann et al. |
| 2003/0086948 A1 | 5/2003 | Benameur et al. |
| 2003/0104048 A1 | 6/2003 | Petal et al. |
| 2003/0175259 A1 | 9/2003 | Karageozian et al. |
| 2003/0180352 A1 | 10/2003 | Patel et al. |
| 2003/0211127 A1 | 11/2003 | Margolin et al. |
| 2004/0009953 A1* | 1/2004 | Comper ............... A61K 31/715 514/54 |
| 2004/0013697 A1 | 1/2004 | Berndl et al. |
| 2004/0033220 A1 | 2/2004 | Hartmann |
| 2004/0057944 A1 | 3/2004 | Galle et al. |
| 2004/0101562 A1 | 5/2004 | Maio |
| 2004/0161423 A1 | 8/2004 | Kumar (Mendiratta) |
| 2004/0202643 A1 | 10/2004 | Margolin et al. |
| 2004/0213847 A1 | 10/2004 | Matharu et al. |
| 2005/0250817 A1 | 11/2005 | Shlieout |
| 2007/0148152 A1 | 6/2007 | Shlieout et al. |
| 2007/0148153 A1 | 6/2007 | Shlieout |
| 2007/0178120 A1 | 8/2007 | Morrison et al. |
| 2008/0019959 A1 | 1/2008 | Becher et al. |
| 2008/0292610 A1 | 11/2008 | Hartmann |
| 2009/0130063 A1 | 5/2009 | Becher et al. |
| 2009/0226414 A1 | 9/2009 | Tijssen et al. |

FOREIGN PATENT DOCUMENTS

| | | |
|---|---|---|
| DE | 2410241 | 9/1975 |
| DE | 2512746 A1 | 9/1976 |
| DE | 2626109 A1 | 12/1976 |
| DE | 2923279 C2 | 11/1980 |
| DE | 3642853 A1 | 6/1988 |
| DE | 4203315 A1 | 8/1992 |
| DE | 4200002 | 7/1993 |
| DE | 4322229 A1 | 1/1995 |
| DE | 4344215 A1 | 6/1995 |
| DE | 19907764 A1 | 11/1999 |
| DE | 19848849 A1 | 4/2000 |
| DE | 19856415 | 6/2000 |
| DE | 10012095 A1 | 9/2000 |
| DE | 29824797 U1 | 2/2002 |
| DE | 69723703 T2 | 1/2004 |
| DE | 60110106 T2 | 3/2006 |
| EP | 0008780 A2 | 3/1980 |
| EP | 0019253 | 11/1980 |
| EP | 0021129 A2 | 1/1981 |
| EP | 0035780 | 9/1981 |
| EP | 0141607 A2 | 5/1985 |
| EP | 0193829 | 9/1986 |
| EP | 0193829 A2 | 9/1986 |
| EP | 0206417 A2 | 12/1986 |
| EP | 0238023 | 9/1987 |
| EP | 0304331 A2 | 2/1989 |
| EP | 0304332 A2 | 2/1989 |
| EP | 0305216 | 3/1989 |
| EP | 0326026 B1 | 8/1989 |
| EP | 0458845 A1 | 8/1990 |
| EP | 0458849 A1 | 8/1990 |
| EP | 0407225 A1 | 1/1991 |
| EP | 0600868 A1 | 12/1991 |
| EP | 0550450 A1 | 2/1992 |
| EP | 0592478 A1 | 1/1993 |
| EP | 0171506 B1 | 9/1993 |
| EP | 0583726 A2 | 2/1994 |
| EP | 0691982 B1 | 1/1996 |
| EP | 0828509 A1 | 12/1996 |
| EP | 0826375 B1 | 3/1998 |
| EP | 0973878 A1 | 10/1998 |
| EP | 0897985 A2 | 2/1999 |
| EP | 1010423 A2 | 6/2000 |
| EP | 1138333 B1 | 4/2001 |
| EP | 1186658 A1 | 3/2002 |
| EP | 1261368 A2 | 12/2002 |
| EP | 1279402 A1 | 1/2003 |
| EP | 0914166 B | 7/2003 |
| EP | 05107472 | 8/2005 |
| EP | 05107474 | 8/2005 |
| EP | 1593688 | 11/2005 |
| EP | 2278002 | 1/2011 |
| FR | 2313916 A1 | 1/1997 |
| GB | 1509866 | 5/1978 |
| JP | 49-036886 | 8/1972 |
| JP | 04936885 | 4/1974 |
| JP | 58148814 A | 9/1983 |
| JP | 58179492 | 10/1983 |
| JP | 59169491 A | 9/1984 |
| JP | 61162185 | 7/1986 |
| JP | 62-029950 | 2/1987 |
| JP | 04-023991 | 1/1992 |
| JP | 4187085 A | 7/1992 |
| JP | 8143457 | 6/1996 |
| JP | 2000-511519 | 5/1997 |
| JP | 09125096 A | 5/1997 |
| WO | WO-8203871 | 11/1982 |
| WO | WO-1987/07292 A1 | 12/1987 |
| WO | WO-1989/08694 A1 | 9/1989 |
| WO | WO-1989/08695 A1 | 9/1989 |
| WO | WO-1991/06638 A1 | 5/1991 |
| WO | WO-91/07948 | 6/1991 |
| WO | WO-81/014454 A1 | 10/1991 |
| WO | WO-91/016060 A1 | 10/1991 |
| WO | WO-91/18623 | 12/1991 |
| WO | WO-92/02617 | 2/1992 |
| WO | WO-1992/12645 A1 | 8/1992 |
| WO | WO-1992/13030 A1 | 8/1992 |
| WO | WO-93/00924 | 1/1993 |
| WO | WO-1993/07260 A1 | 4/1993 |
| WO | WO-1993/07263 A1 | 4/1993 |
| WO | WO-93/18790 | 9/1993 |
| WO | WO-94/08603 | 4/1994 |
| WO | WO-95/07688 | 3/1995 |
| WO | WO-95/08983 | 4/1995 |
| WO | WO-95/15681 | 6/1995 |
| WO | WO-1995/22625 A1 | 8/1995 |
| WO | WO-96/038170 A1 | 12/1995 |
| WO | WO-1996/00343 A1 | 1/1996 |
| WO | WO-1996/16151 A1 | 5/1996 |
| WO | WO-1996/38527 A1 | 12/1996 |
| WO | WO-1997/23605 A1 | 7/1997 |

(56) References Cited

FOREIGN PATENT DOCUMENTS

| | | |
|---|---|---|
| WO | WO-1997/39116 A1 | 10/1997 |
| WO | WO-97/42980 | 11/1997 |
| WO | WO-98/00169 | 1/1998 |
| WO | WO-98/38292 | 9/1998 |
| WO | WO-98/46732 | 10/1998 |
| WO | WO-98/52561 | 11/1998 |
| WO | WO-99/20745 | 4/1999 |
| WO | WO-99/28344 | 6/1999 |
| WO | WO-99/044589 A1 | 9/1999 |
| WO | 1999061002 A1 | 12/1999 |
| WO | WO-2000/01793 A1 | 1/2000 |
| WO | WO-00/34510 | 6/2000 |
| WO | WO-00/54799 | 9/2000 |
| WO | WO-01/01960 | 1/2001 |
| WO | WO-2001/25412 A1 | 4/2001 |
| WO | WO-01/037808 A1 | 5/2001 |
| WO | WO-2001/58276 A2 | 8/2001 |
| WO | WO-01/68139 | 9/2001 |
| WO | WO-2002/20746 A1 | 3/2002 |
| WO | WO-2002/28369 A1 | 4/2002 |
| WO | WO-02/36156 | 5/2002 |
| WO | WO-02/40045 | 5/2002 |
| WO | WO-02/060474 A2 | 8/2002 |
| WO | WO-03/047595 | 6/2003 |
| WO | WO-2003/055967 A1 | 7/2003 |
| WO | WO-2003/080827 A2 | 10/2003 |
| WO | WO-2004/007707 | 1/2004 |
| WO | WO-2004/069872 A1 | 8/2004 |
| WO | WO-2005/12911 | 2/2005 |
| WO | WO-2005/070962 A1 | 8/2005 |
| WO | WO-2005/092370 | 10/2005 |
| WO | WO-2006/044529 A1 | 4/2006 |
| WO | WO-2006/136159 A2 | 12/2006 |
| WO | WO-2007/020260 A2 | 2/2007 |
| WO | WO-2007020259 | 2/2007 |
| WO | WO-2007/135125 | 11/2007 |
| WO | WO-2008/079685 A2 | 7/2008 |

OTHER PUBLICATIONS 2.9.1 Disintegration of Tablets and Capsules, European Pharmacopoeia 5.3, pp. 3351-3353 (2006).
21 C.F.R. 201.302 Notice to manufacturers, packers, and distributors of drugs for internal use which contain mineral oil (1981).
Ammon, et al., "Effect of Lecithin on Jejunal Absorption of Micellar Lipids in Man and on Their Monomer Activity in vitro," Lipds, 14(4):395-400 (1978).
Aptalis Farma S.r.L., Certificate of Inscription in the Regular Identification Data of the Company (Jul. 15, 2011) 4 pages.
Aquacoat ECD—FMC Biopolymer—Bulletin AECD-30—May 18, 1997. RS (1997).
Archibald, A.L. "Comparison of the Serum Amylases of Farm Animals," Compo Biochem. Physiol, vol. 88B (3), pp. 963-968 (1987).
Axcan Pharma, Inc. Viokase Prescibring Information Mar. 2000.
Benzonana, et al., "Etude Cinetique de L'Action de la Lipase Pancreatique Sur Des Triglycerides en Emulsion Essai D'Une Enzymologie en Milieu Heterogene," Biochimica Et Biophysica ACTA, 105:121-136 (1965) (English Abstract).
Bezzine, et al., "Human Pancreatic Lipase: Colipase Dependence and Interfacial Binding of Lid Domain Mutants," Biochemistry, 23:5499-5510 (1999).
Bieger, W. et al., "Two-dimensional isoelectric focusing/sodium dodecyl sulfate gel electrophoresis of protein mixtures containing active or potentially active proteases analysis of human exocrine pancreatic proteins," Anal. Biochem. (1980) 109:222-230.
Biswal, S. et al., "Production variables affecting characteristics of pellets in melt pellitization with wax combination in a laboratory scale spheronizer," Acta Pharm. (2009) 59:199-210.
Borgstrom, "Binding of Pancreatic Colipase to Interfaces; Effects of Detergents," FEBS Letters, 71(2):201-204 (1976).

Borgstrom, "On the Interactions Between Pancreatic Lipase and Colipase and the Substrate and the Importance of Bile Salts," Journal of Lipid Research, 16:411-417 (1975).
Borgstrom, et al., "Pancreatic Juice Co-Lipase: Physiological Importance," Biochimica Et Biophysica ACTA, 242:509-513 (1971).
Borgstrom, et al., "Pancreatic Lipase and Colipase: Interaction and Effect of Bile Salts and Other Detergents," Eur. J. Biochem, 37:60-68 (1973).
Braeuniger et al., Further studies on thermal resistance of bovine parvovirus against moist and dry heat, Int. J. Hyg. Environ. Health, vol. 203 (2000) p. 71-75.
Brewer et al., "Porcine encephalomyocarditis virus persists in pig myocardium and infects human myocardial cells," J. Virology (2001) 75(23):11621-11629.
Carriere, et al., "Quantitative Study of Digestive Enzyme Secretion and Gastrointestinal Lipolysis in Chronic Pancreatitis," Clinical Gastroenterology and Hepatology, vol. 3(1), pp. 28-38 (2005).
Challapalli, K.K. et al., "High reproducibility of large-get two-dimensional electrophoresis," Electrophoresis (2004) 25:3040-3047.
Chemical Abstract, No. 99:200535j, "Capsules Containing Stable Digestive Enzymes", vol. 99, p. 342 (1983).
Chueshov, et al., Industrial Technology of Drugs and Medicine, vol. 2, NFAU Publishing House, pp. 359-362 (2002) [with Translation].
Committee for Proprietary Medicinal Products, Note for Guidance on Virus Validation Studies: The Design, 6 Contribution and Interpretation of Studies Validating the Inactivation and Removal of Viruses, The European Agency for the Evaluation of Medicinal Products, Feb. 14, 1996, p. 1-13.
Copending U.S. Appl. No. 14/074,255, filed Nov. 7, 2013.
Cunningham, L., "Reactivation of Diethyl p-Nitropheoyl Phosphate-Inhibited a-Chymotrypsin by Hydroxylamine," Journal of Biological Chemistry, vol. 207, pp. 443-458 (1954).
Cunningham, N. et al., "Replication of avian infectious bronchitis virus in African green monkey kidney cell line VERO," J. Gen. Virol. (1972) 16:423-427.
D'Costa, D., "Diabetic Neuropathic Cachexia Associated with Malabsorption," Diabetic Medicine, vol. 9/2, pp. 203-205 (1992).
De Fiebre et al. Applied Microbiol. (1969) 17(3): 344-346.
Decision to Revoke the European Patent No. EP1931317 in the Opposition filed by Nordmark against European Patent No. 1931317 dated Nov. 17, 2011.
Defintion of Picornaviridae http://medical-dictionary.thefreedictionary.com/Picornaviridae downloaded Jul. 26, 2011.
Delchier, et al., Fate of Orally Ingested Enzymes in Pancreatic Insufficiency: Comparison of Two.
Delhaye, M., "Comparative Evaluation of a High Lipase Pancreatic Enzyme Preparation and a Standard Pancreatic Supplement for Treating Exocrine Pancreatic Insufficiency in Chronic Pancreatitis," European Journal of Gastronenterology and Hepatology, vol. 8/7, pp. 699-703 (1996).
Derobertis, Cell & Mol. Biol. (1980) 7th Ed., 132-133.
Die Tablette, Handbuch der Entwicklung, Herstellung und Qualitatssicherung, Editiv cantor Verlag Aulendorf (2002) Seiten 85-89, 91-106, 583, 584, WA Ritschel eds. with English translation.
Dimagno, et al., "Fate of Orally Ingested Enzymes in Pancreatic Insufficiency," The New England Journal of Medicine, vol. 296(23), pp. 1318-1322 (1977).
Directive 2003/36/EC of the European Parliament and of the Council of May 26, 2003, Official Journal of the European Union, p. L 156/26-30.
Dony, J. et al., "Etide electrophoretique et immunoelectrophoretigue de preparations enzymatiques injectables: preparation d'origine pancreatique et preparations d'origine testiculaire," progress in Immunological Standardization (1970) 4:395-405, with English translation.
Dutta, et al. "Critical Examination of Therapeutic Efficacy of a pH-Sensitive Enteric-Coated Pancreatic Enzyme Preparation in Treatment of Exocrine Pancreatic Insufficiency Secondary to Cystic Fibrosis," Digestive Diseases and Sciences, vol. 33(10), pp. 1237-1244 (1998).
Enzyme Nomenclature., Recommendations of the Nomenclature Committee of the International Union of Biochemistry and Molecu-

(56) References Cited

OTHER PUBLICATIONS lar Biology on the Nomenclature and Classification of Enzymes by the Reactions they Catalyse, available at http://www.chem.qmul.ac.uk/iubmb/enzyme/.
EP 1931317, Aptalis Pharma S.r.L, Submission of Opponent 02 in Preparation of Oral Proceedings, Aug. 3, 2011.
EP 1931317, Nordmark Arzneimittel GmbH & Co. KG, Submission of Opponent 01 in Preparation of Oral Proceedings, Jul. 20, 2011 (with Translation).
Estes, et al., "Proteolytic Enhancement of Rotavirus Infectivity: Molecular Mechanisms," Journal of Virology, vol. 39(3), pp. 879-888 (1981).
Eurand SA, Notice of Opposition against the European Patent No. EP 1931317, Sep. 23, 2009.
European Patent Appl. No. 06778012.2 Office Action dated Dec. 7, 2010 (5 pages).
European Patent Office Search Report and Opinion for Application No. 07120740.1 dated Mar. 1, 2008.
European Patent Office Search Report and Preliminary Opinion for Application No. 06114329 dated Aug. 1, 2006.
European Patent Office Search Report for Application No. 10178590 dated Dec. 9, 2010.
European Search Report and Preliminary Opinion for European Patent Application No. EP07120740.1 (dated Mar. 3, 2008).
European Search Report for Application No. 97114330 dated Jun. 5, 2002.
European Search Report for European Patent Application No. EP 05733481.5 (dated Oct. 1, 2007).
European Search Report for European Patent Application No. EP93112848 (dated Apr. 15, 1994).
Fallis, LS. et al., "Observations on some metabolic changes after total pancreatoduodenectomy," Annals of Surgery (1948) 639-667.
Fang, et al:, "Purification and Characterization of Adult Diarrhea Rotavirus: Identification of Viral Structural Proteins," Journal of Virology, vol. 63(5), pp. 2191-2197 (1989).
Federal Register, vol. 69(82), Part IV, Apr. 28, 2004.
Fiedler, Herbert P. (Lexikon der Hilfsstoffe fuer Pharmazie, Kosmetik und Angrenzende Gebiete, 5 Aufli. 2002), Encyclopedia of Excipients for Pharmaceuticals, Cosmetics and Related Areas, vol. 5, pp. 733 and 995, including English translation (cover page, pp. 747 & 921) (Total: Six (6) pages). Printed and bound by R. Olden bourg Graphische Betriebe Druckerel GmbH, Kirchheim, Germany.
Fiedler, Herbert P. Encyclopedia of Excipients for Pharmaceuticals, Cosmetics and Related Areas, 5th ed., pp. 1284-1287 (2002).
Gargouri, et al., "Studies on the Detergent Inhibition of Pancreatic Lipase Activity," Journal of Lipid Research, 24:1336-1342 (1983).
Goerg, A et al., "The current state of two-dimensional electrophoresis with immobilized gH gradients," Electrophoresis (2000) 21:1037-1053.
Goldman, D. et al., "Human lymphocyte polymorphisms detected by quantitative two-dimensional electrophoresis," Am. J. Hum. Genet, (1983) 35:827-837.
Goodman & Gilman's "The Pharmacological Basis of Therapeutics," 8th Edition, Pergamon Press (1990) 1471-1477.
Gregory, P.C. "Gastrointestinal pH, Motility/Transit and Permeability in Cystic Fibrosis," J Pediatr Gastroenterol Nutr, vol. 23(5), pp. 513-523 (1996).
Grounds of Appeal in the Opposition filed by Aptalis Pharma S.r.L. against European Patent No. 1931316 dated Jan. 2, 2013.
Guarner, et al., "Fate of Oral Enzymes in Pancreatic Insufficiency," Gut, vol. 34, pp. 708-712 (1993).
Guidance for Industry SUPAC-MR, Modified Release Solid Oral Dosage Forms, Sep. 1997, p. 1-36.
Hogan et al., Pharmaceutical Coating Technology, Chapter 14, pp. 409-39 (1995).
ICH Harmonised Tripartite Guideline, Table of Content and pp. 1-16 (1999).
International Preliminary Report of Patentability for PCT/EP2006/065311 (dated Feb. 20, 2008).
International Preliminary Report of Patentability for PCT/EP2006/065313 (dated Feb. 20, 2008).
International Preliminary Report of Patentability for PCT/EP2007/054880 (dated Nov. 27, 2008).
International Preliminary Report of Patentability for PCT/EP2008/065586 (dated May 18, 2010).
International Preliminary Report on Patentability for Application No. PCT/EP2004/008332 dated Jan. 30, 2006.
International Preliminary Report on Patentability for PCT/EP2006/064717, dated Oct. 11, 2007.
International Search Report and Written Opinion for Application No. PCT/EP2005/051295 dated Jun. 24, 2005.
International Search Report and Written Opinion for PCT/EP2006/064717 (dated Nov. 20, 2006).
International Search Report and Written Opinion for PCT/EP2006/065311 (dated Feb. 2, 2007).
International Search Report and Written Opinion for PCT/EP2006/065313 (dated Feb. 2, 2007).
International Search Report and Written Opinion for PCT/EP2007/054880 (dated Oct. 2, 2007).
International Search Report for Application No. PCT/EP2004/008332 dated Nov. 24, 2004.
International Search Report for Application No. PCT/EP2007/054880 dated Sep. 18, 2007.
International Search Report for Application No. PCT/EP2008/065586 dated Dec. 19, 2008 (and Written Opinion).
International Search Report for PCT/EP2000/002261 (dated Jul. 11, 2000).
International Search Report for PCT/EP2006/064717, dated Nov. 20, 2006.
International Search Report for PCT/EP2008/065586 (dated Dec. 19, 2008).
International Search Report PCT/EP2009/050010 (dated May 7, 2009).
Jenkins, L.W. et al., "Conventional and functional proteomics using large formal two-dimensional gel electrophoresis 24 hours after controlled cortical impact in postnatal day 17 rats," J. Neurotrauma (2002) 19(6):715-740.
Jiang et al., "Biochemical Characterization of the Structural and Nonstructural Polypeptides of a Porcine Group C Rotavirus," Journal of Virology, vol. 64(7), pp. 3171-3178 (1990).
Jones, et al., "Effects of Exogenous Emulsifiers and Fat Sources on Nutrient Digestibility, Serum Lipids, and Growth Performance in Weanling Pigs," J. Anim Sci., 70:3473-3482 (1992).
Kammlott, et al., "Experiments to Optimize Enzyme Substitution Therapy in Pancreatic Duct-Ligated Pigs," Journal of Animal Physiology and Animal Nutrition, 89:105-108 (2005).
Keller et al. Current Treatment Options for Gatroenterology (2003) 6: 369-374.
Keller, et al., "Human Pancreatic Exocrine Response to Nutrients in Health and Disease," Gut, vol. 54(Suppl. VI), pp. vi1-vi28 (2005).
Kirk-Othmer, Encyclopedia of Chemical Technology, 3rd Edition, 23:724-25 (1984).
Klotz, H.P., "Lyophilized pancreatic extract, an aid in the treatment of mild diabetes," La Nouvelle Presse Medicals (1975) 4(32):2333, abstract.
Kobayashi, H. et al., "Susceptibility of Hepatitis B virus to disinfectants or heat," J. Clin. Microbiol. (1984) 20(2):214-216.
Korneeva, et al., "Identification of Catalytically Active Groups of wheat (*Triticum aestivum*) Germ Lipase," Applied Biochemistry and Microbiology, vol. 44(4), pp. 349-355 (2008).
Korzhavykh, et al., "Tablets and Their Various Forms", Russian Pharmacies, No. 19, pp. 1-5 (2010) [with Translation].
Kreon® 25000 Gebrauchsinformation (2007), English Translation.
Layer, et al., "Fate of Pancreatic Enzymes During Small Intestinal Aboral Transit in Humans," The American Physiology Society, pp. G475-G480 (1986).
Layer, et al., "Pancreatic Enzymes in Chronic Pancreatitis," International Journal of Pancreatology, col. 15(1), pp. 1-11 (1994).
Lebowitz, J. et al., "Modem analytical ultracentrifugation in protein science: a tutorial review," Protein Sci. (2002) 11:2067-2079.

(56) References Cited

OTHER PUBLICATIONS

Loa, C.C. et al., "Purification of turkey coronavirus by stephacryl size-exclusion chromatography," J. Virol. Meth. (2002) 104:187-194.
Lukovac, et al., "Gelucire 44/14 Improves Fat Absorption in Rats with Impaired Lipolysis," Biochimica et Biophysica Acta, 1801:665-673 (2010).
Marumerizer QJ—1000T Spheronizer (http://www.lcicorp.com/industrial_granulation/detail/category/marumerizer_qj1000 (accessed Jul. 26, 2013).
Material Safety Data Sheet, Pancreatin 4X USP (10X), Invitrogen Corp., pp. 1-7 (Rev. Apr. 16, 2005).
Maunula, L., "Molecular Epidemiology of Human Rotavirusus—A Study in Genetic Diversity," Academic Dissertation, Haartman Institute, pp. 1-116, Helsinki 2001.
May et al., J. Biol. Standardization (1982) 10:249-259.
McGinity, Aqueous Polymeric Coatings for Pharmaceutical Dosage Forms, pp. 366-67 (1989).
Mclean et al., "Contamination detection in animal cell culture," Encyclopedia of Cell Technology (2000) 1-2:586-598.
Mesiha, M.S. et al., "A screening study of lubricants in wet powder masses suitable for extrusion-spheronization," Drug Dev. & Ind. Pharm. (1993) 19(8):943-959.
Meyer, Boyd Anal. Chem. (1959) 31:215-219.
Michen, et al., "Isoelectric Points of Viruses," Journal of Applied Microbiology, vol. 109, pp. 388-397 (2010).
Murlin et al., "The influence of alkili upon the glycos uria, hyperglycemia and carbon dioxide combining power in human diabetes," Proceedings of the Society for Experimental Biol. Med. (1917) 14:8-9.
Murthy, et al., "In Vitro Release Characteristics of Hard Shell Capsule Products Coated with Aqueous- and Organic-Based Enteric Polymers," Journal of Biomaterials Application, J. Biomater Appl., vol. 3, pp. 52-79 (1988), available at http://jba.sagepub.com.
Naftifine HCl MSDS (Jun. 23, 2004), available at http://pharmacycide.com/msds/Naftifine_HCL.
Nakamura, et al., Pancreas, vol. 16(3), pp. 329-336.
Nilsson, et al., "Biosynthesis and morphogenesis of group C rotavirus in swine testicular cells," Arch. Virol., vol. 133, pp. 21-37 (1993).
Nishihara, J.C. et al., "Quantitative evaluation of proteins in one- and two-dimensional polyacrylamide gels using a fluorescent stain," Electrophoresis (2002) 23:2203-2215.
Nordmark Arzneimittel GmbH & Co. KG, Notice of Opposition against the European Patent No. EP 1931317, Aug. 6, 2009 with translation.
Notice of Opposition, EP1931316, Eurand S.p.A., Nov. 15, 2010 (12 pages).
Notices of Oppagation Filed by Nordmark Arzneimittel GmbH & Co. KG and Eurand S.p.A, EP 1931317; Reply of the Patent Proprietor to the Notice of Opposition.
O'Doherty, et al., "Role of Luminal Lecithin in Intestinal Fat Absorption," Lipids, 8{5}:249-255 (1972).
Oshima, et al., "Preparation of Rapidly Disintegrating Tablets Containing Itraconazole Solids Dispersion," Chem. Pharm. Bull., vol. 55(11), pp. 1557-1562 (2007).
Overland, et al., "Effect of Lecithin on the Apparent Ileal and Overall Digestibility of Crude Fat and Fatty Acids in Pigs," J. Anim Sci, 72:2022-2028 (1994).
Padfield, P.J. et al., "The use of two-dimensional gel electrophoresis and high-performance liquid chromatography for the analysis of pancreatic juice," The Pancreas: Biology, Pathbiology, and Disease, Second Edition, Chapter 14 (1993) 265-273.
Pancreatic Enzyme Preparations, Aliment. Pharmacol. Therap., vol. 5, pp. 365-378 (1991).
Pariza, M. W. et al., "Evaluating the safety of microbial enzyme preparations used in food processing: update for a new century," Regul. Toxicol. Pharmacol. (2001) 33(2):173-186.
PEG 4000, EM Grade, Technical Data Sheet 279, Polysciences, Inc. (1999) 2 pages.
Pharmaceutical Excipients, 5th edition, Cetyl Alcohol (2006) 155-56.
Pharmazeutische Technologie, Georg Thieme Verlag Stuttgart (1978/1991) 2: 178-179, with English translation.
Porter, S.C., "Coating of pharmaceutical dosage forms," Chapter 46, Remington: The Science and Practice of Pharmacy, Lippincott, Williams & Wilkins, Philadelphia (2005) 21st Edition, Chapter 46:929-938.
Reed et al., "A simple method of estimating fifty per cent endpoints," Amer. J. of Hygiene, vol. 27 (3), pp. 493-497 (May 1938).
Register of Pharmaceuticals in Russia, RP-Pharmacist, Annual Collection, Issue 5, pg. 772 (2003) [with Translation].
Remington, The Science and Practice of Pharmacy, 20th ed., pp. 326 and 1035-1036 (2000).
Reply from Opponent in the Opposition filed by Nordmark against European Patent No. 1931317 dated Jul. 20, 2012.
Reply from Opponent in the Opposition filed by Nordmark against European Patent No. 1931317 dated Jul. 20, 2012, with English translation.
Reply of Proprietor in the Opposition filed by Aptalis Pharma S.r.L. against European Patent No. 1931316 dated Jun. 7, 2011.
Reply to Appeal in the Opposition filed by Aptalis Pharma S.r.L. against European Patent No. 1931316 dated May 13, 2013.
Reply to Appeal in the Opposition filed by Nordmark Against European Patent No. 1931317 dated Sep. 28, 2012.
Reply to Summons to Attend Oral Proceedings: filing of new main claim request in the Opposition filed by Aptalis Pharma S.r.L. against European Patent No. 1931316 dated Feb. 23, 2012.
Reply to Summons to Attend Oral Proceedings: New Written Submissions and Claim Amendments in the Opposition filed by Nordmark against European Patent No. 1931317 dated Aug. 4, 2011.
Results and Minutes of Oral Proceedings in the Opposition filed by Aptalis Pharma S.r.L. against European Patent No. 1931316 dated Sep. 5, 2012.
Results and Minutes of Oral Proceedings in the Opposition filed by Nordmark against European Patent No. 1931317 dated Oct. 6, 2011.
Reynolds, "A New Technique for the Production of Spherical Particles," Manufact. Chemist & Aerosol News, pp. 40-43 (Jun. 1970).
Ridder, G. et al., "Quantitative analysis of pattern recognition of two-dimensaional electrophoresis gels," Clin. Chem. (1984) 30(12):1919-1924.
Rompp Chemie Lexikon, Jurgen Falbe et al, editors, (1992) Georg Thieme Verlag, 9:3532 "Polyethylenglykole", with English translation.
Sachs-Barrable, et al., "Lipid Excipients Peceol and Gelucire 44/14 Decrease P-Glycoprotein Mediated Efflux of Rhodamine 123 Partially Due to Modifying P-Glycoprotein Protein Expression within Caco-2 Cells," J Pharm Pharmaceut Sci, vol. 10(3), pp. 319-331 (2007).
Saif et al., "Serial Propagation of Porcine Group C Rotavirus (Pararotavirus) in a Continuous Cell Line and Characterization of the Passaged Virus," Journal of Clinical Microbiology, vol. 26(7), pp. 1277-1282 (1988).
Sanekata, et al., "Isolation of Group B Porcine Rotavirus in Cell Culture," Journal of Clinical Microbiology, vol. 34(3), pp. 759-761 (1996).
Saunders, et al., "Lecithin Inhibits Fatty Acid and Bile Salt Absorption from Rat Small Intestine In Vivo," Lipids, 11 (12):830-832 (1976).
Savage et al., "Determination of Adequate Moisture Content for Efficient Dry-Heat Viral Inactivation in Lyophilized Factor VIII Loss on Drying and by Near Infrared Spectroscopy," Biologicals, vol. 26, pp. 119-124 (1998).
Scharpe, S. et al., "Isoelectric characterization of porcine pancreative alpha amylases," Journal De Pharmacie De Belgique (1973) 28(6):705-708.
Scheele, G.A., "Two-dimensional gel analysis of soluble proteins," J. Biol. Chem. (1975) 250(14):5375-5385.
Shimura, K. et al., "Affinophoresis in two-dimensional agarose gel electrophoresis specific separation of biomolecules by a moving affinity ligand," Anal. Biochem. (1987) 161(1):200-206.

(56) References Cited

OTHER PUBLICATIONS

ShinEtsu Chemical Company, USP Hypromellose Phthalate Enteric Coating Material (Sep. 2002) 10 pages.
Simek, I., "Substitution Therapy in Insufficient External Pancreatic Secretion," Online Medline Databse (1993).
Smolka, M. et al,, "Quantitative protein profiling using two-dimensional gel electrophoresis, isotope-coded affinity tag labeling, and mass spectrometry," Mol. Cell Proteomics (2002) 1.1:19-29.
Sofer, et al , "Part 6, Inactivation Methods Grouped by Virus," BioPharm Internationals, S-37-42 (2003).
Spearman, C., "The method of 'right and wrong cases' ('constant stimuli') without Gauss's formulae," Brit. J. Psych. (1908) vol. II, Part 3,227-242.
Subramanian et al., "Effect of lipid excipients on in vitro pancreatic lipase activity," Drug Dev. Ind. Pharm., vol. 29(8), pp. 885-890 (2003).
Sucker et al., "Pharmazeutische Techologie," pp. 273-283 (1991) with translation.
Summons to Oral Proceedings in the Opposition filed by Aptalis Pharma S.r.L. against European Patent No. 1931316 dated Dec. 22, 2011.
Summons to Oral Proceedings in the Opposition filed by Nordmark Arzneimittel GmbH against European Patent No. 1931317 dated Mar. 29, 2011.
Sun et al., "Fluidized-bed spray coated porous hydrogel beads for sustained release of diclofenac sodium," Journal of Controlled Release, vol. 47, pp. 247-260 (1997).
Tabasi, S.H. et al., "Quality by design, Part I: Application of NIR spectroscopy to monitor tablet manufacturing process," J. Pharm. Sci. (2008) 97:4040-4051.
Tabasi, S.H. et al., "Quality by design, Part II: Application of NIR spectroscopy to monitor the coating process for a pharmaceutical sustained release product," J. Pharm. Sci. (2008) 97:4052-4066.
Tabashi, S.H. et al., "Quality by design, Part III: Study of curing process of sustanied release coated products using NIR spectroscopy," J. Pharm. Sci. (2008) 97:4067-7086.
Tabeling, et al., "Studies on Nutrient Digestibilities (Pre-Caecal and Total) in Pancreatic duct-Ligated Pigs and the Effects of Enzyme Substitution," J. Anim. Physiol. A. Anim. Nutr. 82:251-263 (1999).
Technical Reports on Comparative Exp.x, examples 117 thru 717 (2009), including 8810586 "PEG4000 iprop high"; 8810587 "PEG2000"; 8810588 "PEG8000"; 8810589 "HPMC iprop equ"; 8810590 "PVP iprop equ"; 8810591 "HPMC iprop high"; and 8810592 "PVP iprop low".
The Ministry of Health, Labour and Welfare Ministerial Notification No. 285, Japan Pharmacopoeia, 8 pages (2006).
Thoma et al., "Influence of aqueous coatings on the stability of enteric coated pellets and tablets," European Journal of Pharmaceutics and Biopharmaceutics, vol. 47, pp. 39-50 A286(1999).
Thomson et al., Ch. 73 Porcine parvovirus infection, Infectious Diseases of Livestock vol. 2 (2nd ed. 2004) p. 806-814.
Tischer et al., "Replication of procine circovirus: induction by glucosamine and cell cycle dependence," Archives of Virology, vol. 96, pp. 39-57 (1987).
Tsunemitsu, et al., "Isolation, Characterization, and Serial Propagation of a Bovine Group C Rotavirus in a Monkey Kidney cell Line (MA1 04)," Journal of Clinical Microbiology, vol. 29(11), pp. 2609-2613 (1991).
Turner et al., The Inactivation of Viruses in Pig Slurries: A Review, Bioresource Technology, vol. 61 (1997) p. 9-20.
U.S. Patent Office Action for U.S. Appl. No. 11/464,704 dated Apr. 25, 2014 (25 pages).
U.S. Patent Office Action for U.S. Appl. No. 11/464,754 dated Apr. 23, 2014 (31 pages).
U.S. Patent Office Notice of Allowance for U.S. Appl. No. 11/085,073 dated Apr. 1, 2014 (17 pages).
U.S. Pharmacopeia 28, National Formulary 23, 23rd Edition, (2004) 10 pages.
Ueba, O., "Respiratory synctial virus. I. Concentration and purification of the infectious virus," Acta Medica Okayama (1978) Article 2, 32(4):265-272.
Ullman's Encyclopedia, pp. 179, 180 and 199 (1987).
U.S. Appl. No. 60/708,526 by George Shlieout et al., filed Aug. 15, 2005.
United States Patent Office Action for U.S. Appl. No. 11/085,073 dated Apr. 7, 2008 (17 pages).
United States Patent Office Action for U.S. Appl. No. 11/085,073 dated Feb. 26, 2010 (19 pages).
United States Patent Office Action for U.S. Appl. No. 11/085,073 dated Jul. 13, 2007 (13 pages).
United States Patent Office Action for U.S. Appl. No. 11/085,073 dated Oct. 23, 2006 (12 pages).
United States Patent Office Action for U.S. Appl. No. 11/464,704 dated Aug. 2, 2013 (21 pages).
United States Patent Office Action for U.S. Appl. No. 11/464,704 dated Aug. 21, 2009.
United States Patent Office Action for U.S. Appl. No. 11/464,704 dated Jul. 28, 2015 (26 pages).
United States Patent Office Action for U.S. Appl. No. 11/464,704 dated May 26, 2010.
United States Patent Office Action for U.S. Appl. No. 11/464,754 dated Aug. 16, 2013 (26 pages).
United States Patent Office Action for U.S. Appl. No. 11/464,754 dated Jun. 1, 2010 (16 pages).
United States Patent Office Action for U.S. Appl. No. 11/464,754 dated Sep. 2, 2009 (18 pages).
United States Patent Office Action for U.S. Appl. No. 11/751,497 dated Apr. 17, 2013 (16 pages).
United States Patent Office Action for U.S. Appl. No. 11/751,497 dated Jul. 14, 2010.
United States Patent Office Action for U.S. Appl. No. 11/751,497 dated Mar. 10, 2011 (8 pages).
United States Patent Office Action for U.S. Appl. No. 11/751,497 dated Nov. 12, 2009 (12 pages).
United States Patent Office Action for U.S. Appl. No, 11/751,497 dated Oct. 21, 2013 (13 pages).
United States Patent Office Action for U.S. Appl. No. 111/751,497 dated May 22, 2015 (12 pages).
United States Patent Office Action for U.S. Appl. No. 12/271,480 dated Jan. 6, 2015 (15 pages).
United States Patent Office Action for U.S. Appl. No. 12/271,480 dated Jul. 14, 2011 (12 pages).
United States Patent Office Action for U.S. Appl. No. 12/271,480 dated May 24, 2013 (14 pages).
United States Patent Office Action for U.S. Appl. No. 12/271,480 dated Nov. 3, 2010.
United States Patent Office Action for U.S. Appl. No. 12/271,480 dated Sep. 19, 2013 (13 pages).
United States Patent Office Final Rejection for U.S. Appl. No. 12/271,480 dated Jul. 20, 2015 (13 pages).
United States Patent Office Notice of Allowance for U.S. Appl. No. 11/464,754 dated Jul. 27, 2015 (17 pages).
United States Pharmacopoeia for Pancrelipase Delayed-Release Capsules (2 pages) (2006).
United States Pharmacopoeia Method 711 Dissolution (18 pages) (2006).
USP 32, NF 27, Pancrelipase Delayed-Release Capsules (2009).
V An Den Bergh, G. et al., "Fluorescent two-dimensional difference gel electrophoresis and mass spectrometry identity age-related protein expression differences for the primary visual cortex of kitten and adult cat," J. Neurochem. (2003) 85:193-205.
Veronese, et al., "Photoinactivation of Enzymes by Linear and Angular Furocoumarins," Photochernistry and Photobiology, vol. 36(1), pp. 25-30 (1982).
Villegas et al., "A rapid method to produce high yields of purified rotavirus particles," J. Virol. Meth. (2002) 104:9-19.
Voss, T. et al,, "Observations on the reproducibility and matching efficiency of two-dimensional electrophoresis gels: consequences for comprehensive data analysis," Electrophoresis (2000) 21:3345-3350.

(56) References Cited

OTHER PUBLICATIONS

Wallis, et al., "Plaque Enhancement of Enteroviruses by Magnesium Chloride, Cysteine, and Pancreatin," Journal of Bacteriology, vol. 91(5), pp. 1932-1935 (1996).
Walsh, et al., "Tryosinogen and Chymotrypsinogen as Homologous Proteins," PNAS, vol. 52, pp. 884-889 (1964).
Wan et al., "Plasticizers and their effects on microencapsulation process by spray-drying in an aqueous system," J. Microencapsulation, vol. 9(1), pp. 53-62 (1992).
Watkins, Paul, "The Barrier Function of CYP3A4 and P-Glycoprotein in the Small Bowel," Advanced Drug Delivery Reviews, vol. 27, pp. 161-170 (1997).
Worthington Enzyme Manual, Lipase (1993), pp. available at http://www.worthington-biochem.com/PL/default.html (2 pages).
Worthington Enzyme Manual, Trypsin (1993), pp. available at http://www.worthington-biochem.com/TRY/default.html (3 pages).
Worthington Enzyme Manual, Trypsinogen (1993), pp. available at http://www.worthington-biochem.com/TG/default.html (1 pages).
Written Opinion for Application No. PCT/EP2006/065311 dated Feb. 2, 2007.
Written Opinion for Application No. PCT/EP2007/054880 dated Sep. 18, 2007.
Written Submission by Aptalis Pharma S.r,L. in the Opposition filed by Aptalis Pharma S.r.L. against European Patent No. 1931316 dated Mar. 12, 2012.
Written Submission by Opponent in the Opposition filed by Aptalis Pharma S.r.L. against European Patent No. 1931316 dated May 4, 2012.
Written Submission in the Opposition filed by Nordmark against European Patent No. 1931317 dated Aug. 25, 2011, with English translation.
The Japanese Pharmacopoeia. Tokyo: Society of Japanese Pharmacopoeia: Distributed by Yakuji Nippo, 1996, preface, table of contents, pp. 1-3, 961-962.
Praxis der Sterilisation, Wallhaussers (ed.), pp. 83-84 and 86-87, 1995.
Praxis der Sterilisation, Wallhaussers (ed.), p. 34, 2003.
"Pancreatin," The Japanese Pharmacopoeia, Fourteenth Edition. Tokyo: Society of Japanese Pharmacopoeia: Distributed by Yakuji Nippo, 2001, 10 pages.
"Pancreatin," The Japanese Pharmacopoeia, Fifteenth Edition. Tokyo: Society of Japanese Pharmacopoeia: Distributed by Yakuji Nippo, 2006, 8 pages.
Sidwell, R.W., et al., "Procedure for the Evaluation of the Virucidal Effectiveness of an Ethylene Oxide Gas Sterilizer," Applied Micrbiology, 1969, vol. 17(6), pp. 790-796.
The International Conference for Harmonisation of Technical Requirements for Pharmaceuticals for Human Use (ICH), ICH Harmonised Tripartite Guideline—Viral Safety Evaluation of Biotechnology Products Derived from Cell Lines of Human or Animal Origin, Q5A(R1), Sep. 23, 1999, 31 pages.
Study Report: Exactly reproducing of the japan patent application JP49-36885A, by Abbott Products GmbH, 10 pages.
Notice of Appeal of Decision to Revoke the European Patent No. 1913138 in the Opposition filed by Nordmark, dated Mar. 19, 2019, 24 pages.
Reply of the Patent Proprietor to Notice of Opposition filed by Nordmark against European Patent No. 2278002, dated Oct. 10, 2018, 13 pages.
Reply of the Patent Proprietor to Notice of Opposition filed by Nordmark against European Patent No. 1913138, dated Nov. 6, 2017, 9 pages.
Decision to Revoke the European Patent No. 1913138 in the Opposition filed by Nordmark, dated Nov. 9, 2018, 23 pages.
"Pancreas Powder," European Pharmacopoeia, 6th Edition, 6.2 Supplement. Council of Europe (COE): Strasbourg Cedex, France, 2007, 7 pages.
Kreon® 25000, magnified photogaph 2009.

* cited by examiner

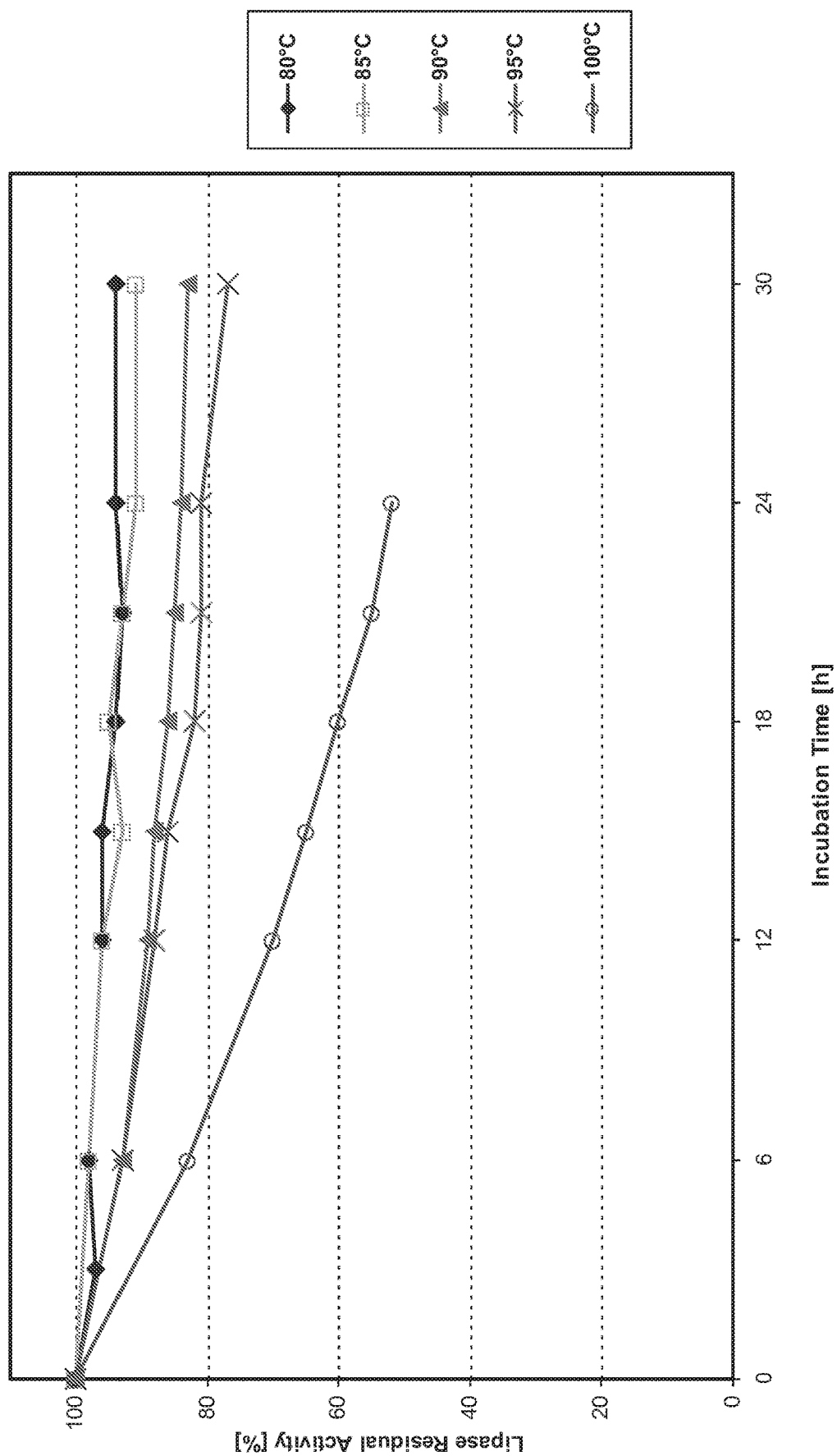
Figure 1: Lipase activity after heating pancreatin at 80°C, 85°C, 90°C, 95°C and 100°C with a solvent content of 1%.

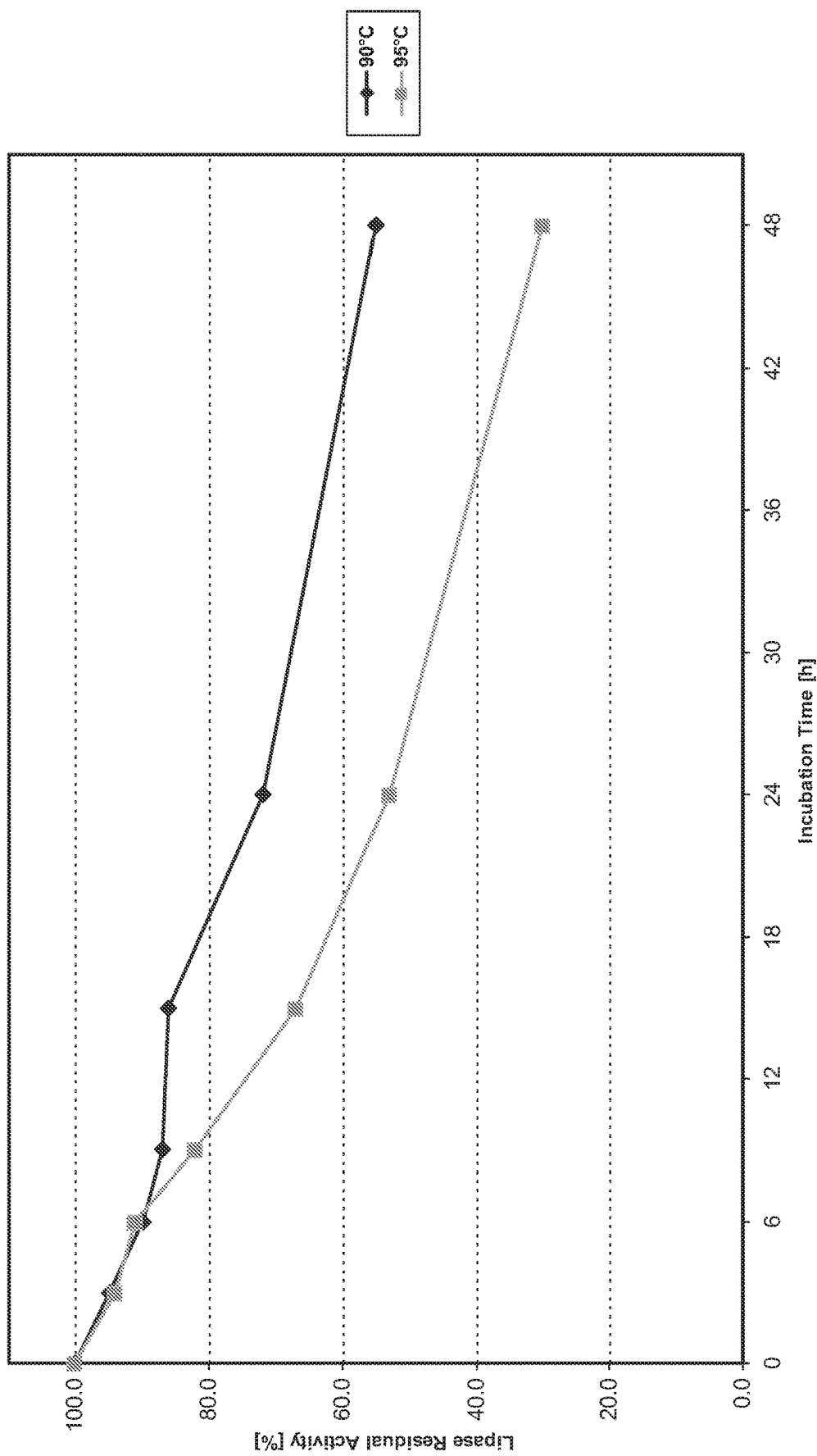

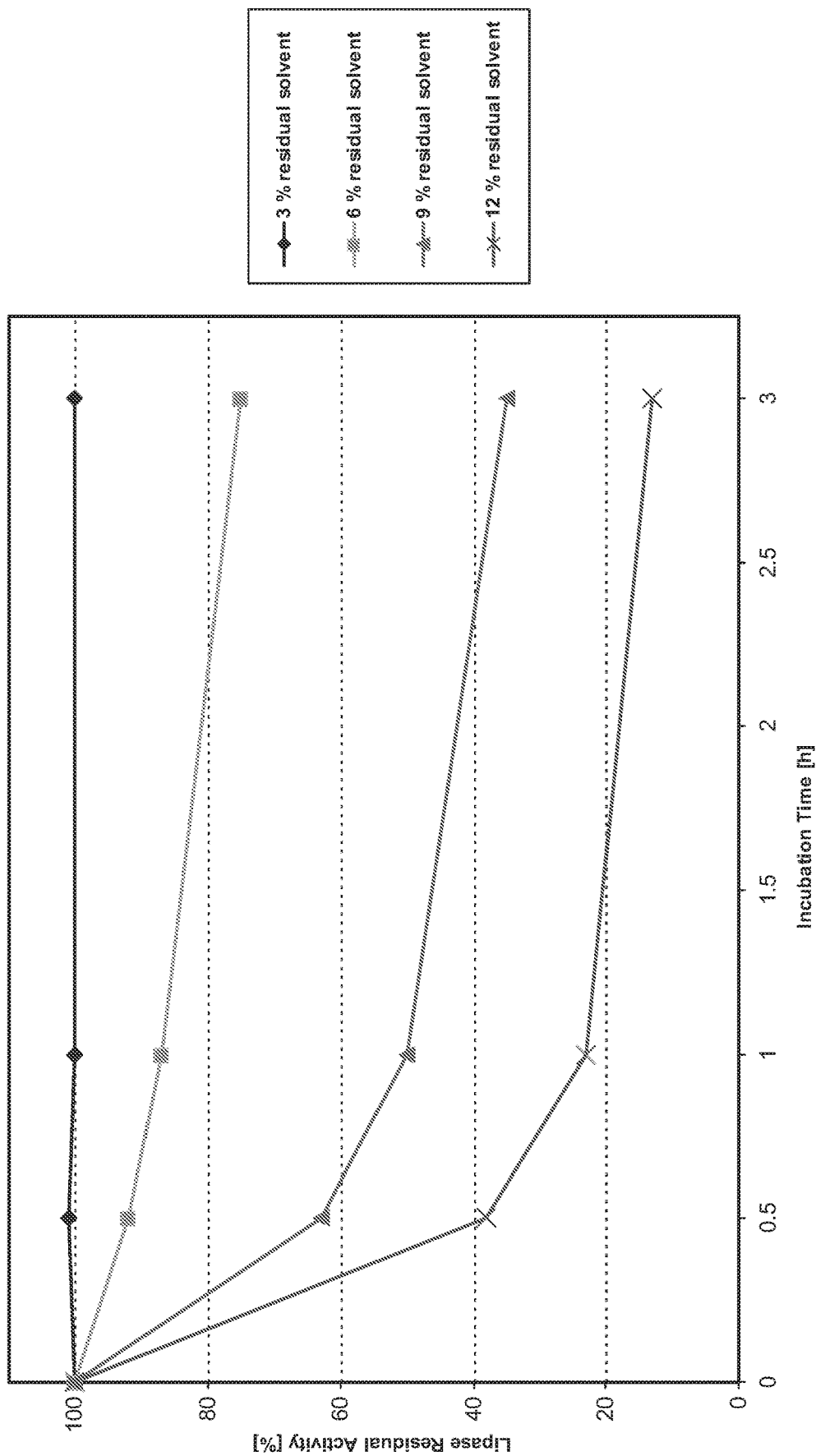

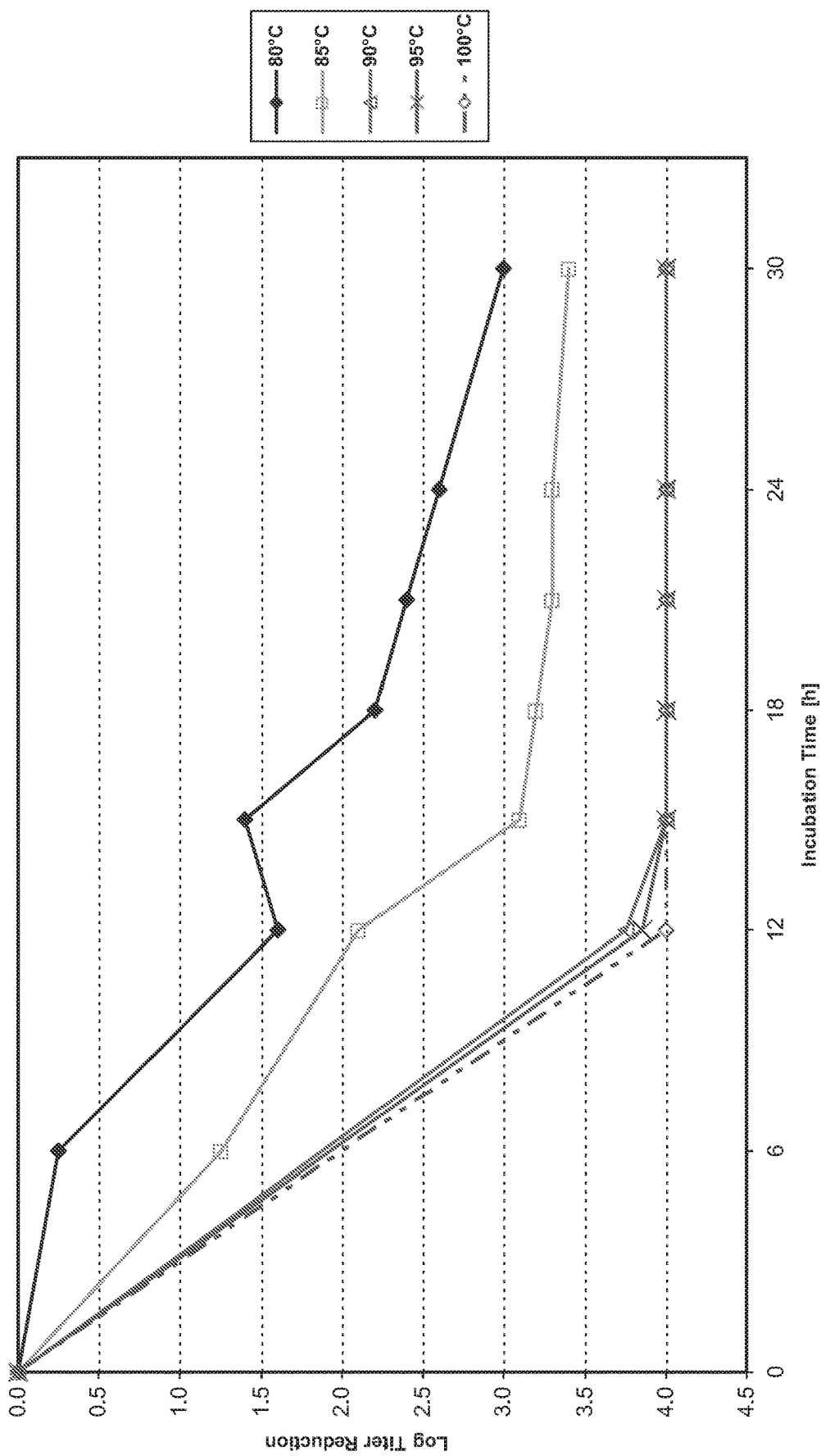

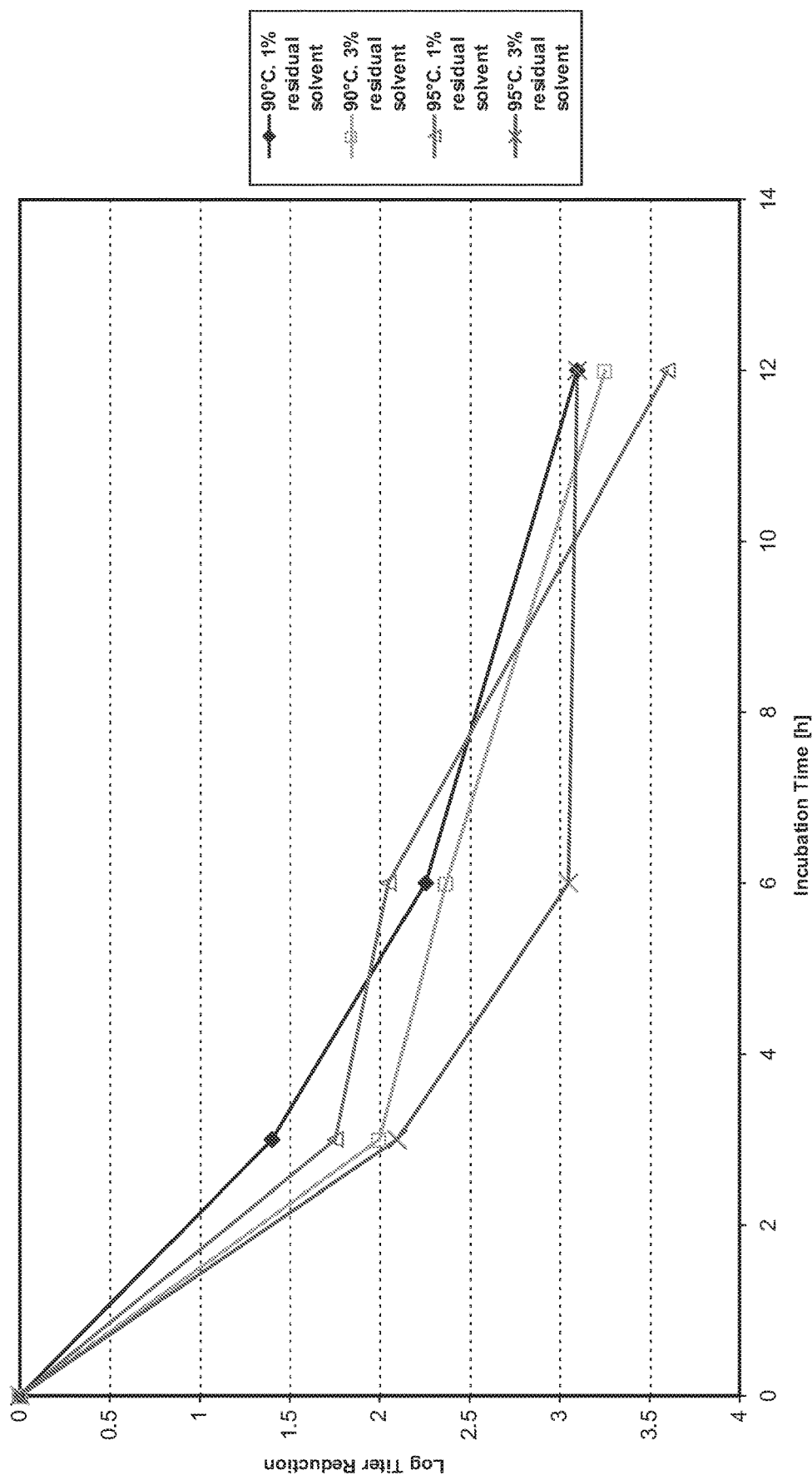

PROCESSES FOR THE MANUFACTURE AND USE OF PANCREATIN

CROSS-REFERENCE TO RELATED APPLICATIONS

This application is a continuation of U.S. patent application Ser. No. 11/460,330, file Jul. 27, 2006, which claims the benefit of U.S. Provisional Application No. 60/703,813 filed Jul. 29, 2005, the contents of which are incorporated by reference in their entirety.

FIELD OF THE INVENTION

Described herein is a process for the manufacture and use of pancreatin in which the concentration of one or more viral contaminants therein is reduced by heating the pancreatin.

BACKGROUND

Pancreatin is a substance which is derived from mammalian pancreas glands and comprises different digestive enzymes such as lipases, amylases and proteases. Pancreatin has been used to treat pancreatic exocrine insufficiency which is often associated with cystic fibrosis, chronic pancreatitis, post-pancreatectomy, post-gastrointestinal bypass surgery (e.g. Billroth II gastroenterostomy) and ductal obstruction from neoplasm (e.g. of the pancreas or common bile duct). For the application of pancreatin in pharmacological products it is preferred to substantially maintain the intrinsic high level of activity of the different digestive enzymes. However, these enzymes can be subject to degradation, e.g., upon storage, and are particularly sensitive to elevated temperatures. Thus, pancreatin requires carefully controlled conditions during the overall handling, manufacturing and storage process.

Due to the animal origin of pancreatin, this may further comprise other components which are unwanted such as one or more biological contaminants. During more than 100 years of commercialization of pharmaceutical products containing pancreatin, no case has been reported where patients have been affected by pancreatin contaminated by any virus. However, companies producing pharmaceutical products derived from biological tissues and/or body fluids experience increasing pressure from the regulatory bodies to increase the level of safety of their products by reducing all kinds of contaminants to the lowest level possible, independent of whether any concerned contaminant is considered a human pathogen or not. For the application of pancreatin in pharmacological products, it is therefore desirable to minimize the concentration of biological contaminants therein down to generally accepted detection limits.

Hence, for the manufacturing, handling and storage process of pancreatin, the skilled person is faced with the challenge of tailoring such processes in a way that a high level of activity of the different digestive enzymes is maintained while at the same time the concentration of one or more biological contaminants therein is minimized.

The current manufacturing processes of pancreatin would not seem to allow efficient inactivation of biological contaminants, in particular of specific viruses.

Different approaches are known to reduce the concentrations of viruses and bacteria within enzymatic compositions. Such methods include heat treatment, filtration, the addition of chemical inactivants or sensitizers, treatment with irradiation and extended heating. These methods are described below.

Heat treatment implies that the product e.g. be heated to 60° C. for 70 hours which can be damaging to sensitive products. In some instances, conventional heat inactivation can actually destroy a substantial amount of the enzymatic activity of a product.

Filtration involves filtering the product in order to physically remove contaminants. Unfortunately, this method may also remove products having a high molecular weight. Further, in certain cases, small viruses and similarly sized contaminants and pathogens may not be removed by the filter.

The procedure of chemical sensitization involves the addition of noxious agents which bind to the DNA/RNA of the virus and which are activated by either UV or other radiation. The radiation produces reactive intermediates and/or free radicals which bind to the DNA/RNA of the virus, break the chemical bonds in the backbone of the DNA/RNA, and/or crosslink or complex it in such a way that the virus can no longer replicate. This procedure requires unbound sensitizer to be washed from products since the sensitizers are toxic, if not mutagenic or carcinogenic, and cannot be administered to a patient.

U.S. Pat. No. 3,956,483 (Lewis) discloses a method of preparing pancreatin having suitable amylolytic, proteolytic and lipolytic activities and of eliminating harmful bacteria therefrom while maintaining said activities. Said method comprises heating the pancreatin to a sufficiently high temperature between 120° F. and 180° F. (approx. 49-82° C.). Lewis, however, fails to provide a process which would be suitable to minimize the concentration of viruses down to presently accepted detection limits.

U.S. Pat. No. 6,749,851 (Mann) suggests the treatment of compositions comprising digestive enzymes by stabilizing the compositions in a first step by either (a) reducing the temperature of, (b) reducing the solvents of, or (c) adding a stabilizer to the composition, followed by irradiation of the composition in a second step.

Braeuniger et al. (Braeuniger et al., Int. J. Hyg. Environ. Health 203, 71-75, 2000) suggest the use of heat for the inactivation of the bovine parvovirus. It has been demonstrated that the bovine parvovirus which can be deactivated is dependent upon exposure and residual moisture. In general, higher moisture contents allow shorter heat exposure durations providing the same inactivation as a lower moisture content in combination with a longer exposure duration. However, Braeuniger et al. do not disclose anything about the effect that heat has on enzymes such as lipases, amylases and proteases forming part of animal pancreatin. Thus, there is a need for a process which provides pancreatin having enzymes with a high level of activity while sufficiently reducing the concentration of biological contaminants.

It has now been found that select conditions can be employed in the manufacture of pancreatin in which the concentration of one or more biological contaminants therein has been reduced and in which the enzyme activity is maintained at an acceptable level. In particular, it has been found that a process as disclosed and claimed herein is useful to decrease the concentration of viral contaminants in pancreatin. Furthermore, the process described herein has been found to effectively meet various regulatory requirements regarding the removal of viruses from biological products (e.g. "Note For Guidance on Virus Validation Studies: The Design, Contribution and Interpretation of Studies Validating the Inactivation and Removal of Viruses", issued from the Committee For Proprietary Medicinal Products (herein after referred to as "CPMP/BWP/268/95"))

while at the same time maintaining enzyme activities (e.g. lipase, protease and amylase) at an acceptable level.

Another advantage of the process described herein, and the resulting pancreatin, as well as the pharmaceutical compositions comprising the pancreatin obtained by the process described herein, is its applicability for laboratory scale, pilot scale and production scale.

SUMMARY

Accordingly, one embodiment disclosed herein is a process for the manufacture of pancreatin in which the concentration of one or more biological contaminants, in particular of viral contaminants, has been reduced by heating the pancreatin for a period up to about 48 hours at a temperature of at least 85° C. wherein the solvents in the pancreatin are less than about 9% by weight at any point during the heating step. Such process provides pancreatin, in which the enzyme activity is maintained at an acceptable level and in which the concentrations of one or more biological contaminants, in particular of one or more viral contaminants, are reduced. Described herein is a process for the manufacture of pancreatin, comprising heating a dispersed form of pancreatin containing one or more solvents at a temperature of at least 85° C. for a period of up to about 48 hours, and wherein the total amount of solvents present in the pancreatin is less than about 9% by weight at any point during the heating step.

Another embodiment disclosed herein is a process for manufacturing a pharmaceutical composition comprising pancreatin, in accordance with the disclosed process wherein such pharmaceutical composition is in a dosage form suitable for oral administration and for immediate and/or modified release, such dosage form can be selected from tablets, microtablets, pellets, micropellets, microspheres, granules, granulates, powders, suspensions, emulsions, dispersions, capsules, sachets as well as other dosage forms.

Another embodiment is a pharmaceutical composition comprising
(1) a pharmacologically effective quantity of pancreatin wherein said pancreatin has been heated in the form of a dispersed pancreatin containing one or more solvents, wherein the total amount of solvents present in the pancreatin is less than about 9% by weight at any point during the heating step, to a temperature of at least 85° C.; wherein the titer level of a viral contaminant present in the pancreatin after heating is at least about 1000 times less than the titer level of the viral contaminant present in the pancreatin prior to heating; and
(2) one or more pharmaceutically acceptable excipients.

Another embodiment is directed to a pharmaceutical composition in the form of a capsule or sachet wherein the capsule or sachet comprises pancreatin subjected to the disclosed process.

Another embodiment is directed towards a method of treating pancreatic exocrine insufficiency by administering a safe and effective amount of pancreatin obtained by the process described herein.

Other objects, features and advantages will be set forth in the detailed description of embodiments that follows, and in part will be apparent from the description or may be learned by practice of the claimed invention. These objects and advantages will be realized and attained by the processes and compositions particularly pointed out in the written description and claims hereof.

BRIEF DESCRIPTION OF THE DRAWINGS

FIG. 1: Lipase activity after heating pancreatin at temperatures of 80° C., 85° C., 90° C., 95° C. and 100° C. with a solvent content of 1%. The lipase activity was determined after 2, 4, 6, 12, 15, 18, 21, 24 and 30 hours.

FIG. 2: Lipase activity after heating pancreatin at temperatures of 90° C. and 95° C. with a solvents content of 3%. The lipase activity was determined after 2, 4, 8, 15, 24 and 48 hours.

FIG. 3: Lipase activity after heating pancreatin at a temperature of 80° C. having a solvent content of 3%, 6%, 9% and 12%. The lipase activity was determined after 0.5, 1.0 and 3.0 hours.

FIG. 4: Log titer reduction of porcine pancreatin spiked with porcine parvovirus (hereinafter referred to as "PPV-spiked pancreatin") at temperatures of 80° C., 85° C., 90° C., 95° C. and 100° C. having a solvent content of 1%. The virus concentration was determined after 6, 12, 15, 18, 21, 24 and 30 hours.

FIG. 5: Log titer reduction of PPV-spiked pancreatin at temperatures of 90° C. and 95° C. having a solvent content of 1% and 3% for a period of 12 hours. The virus concentration was determined after 3, 6 and 12 hours.

DETAILED DESCRIPTION

Unless defined otherwise, all technical and scientific terms used herein are intended to have the same meaning as is commonly understood by one of ordinary skill in the relevant art.

As used herein, the term "sterilize" is intended to mean a reduction in the concentration of at least one biological contaminant found in pancreatin, in particular dispersed pancreatin, being subjected to the process described herein. More specifically, the term "sterilize" is intended to mean a reduction in the concentration of at least one viral contaminant found in pancreatin, in particular dispersed pancreatin, being subjected to the process described herein.

As used herein, the term "pancreatin" is intended to mean pancreatin originating from any mammalian pancreas glands, such as bovine and porcine pancreatins. For example, pancreatin which is produced according to the processes described in U.S. Pat. No. 4,623,624 or according to analogous processes may be used for the purposes of the present disclosure. To achieve the preferred results of decreasing the biological contaminants in the pancreatin, the use of a dispersed form of pancreatin which is compatible with the process conditions described herein is preferred. Dispersed forms of pancreatin comprise e.g. powders, pellets, micropellets, microspheres, granules and granulates. Preferred results are achieved with pancreatin powders, e.g. pancreatin powders directly obtained from a process to produce pancreatin. The pancreatin as used herein may also comprise one or more pharmaceutically acceptable excipients which are compatible with the process conditions as described herein and which may be e.g. selected from the pharmaceutically acceptable excipients provided below.

As used herein, the term "biological contaminant(s)" is intended to mean a contaminant that, upon direct or indirect contact with pancreatin, may have a deleterious effect on the pancreatin or upon a recipient thereof. Furthermore, the term "active biological contaminant" is intended to mean a biological contaminant that is capable of causing a deleterious effect, either alone or in combination with another factor, such as a second biological contaminant, in the preparation of pancreatin or to the recipient of the pancreatin. Such biological contaminants include, but are not limited to, viral contaminants and/or germs. Germs include, but are not limited to, bacteria, molds and/or yeasts. A biological contaminant may be a human pathogen.

As used herein, the term "virus" or "viral contaminant(s)" is intended to mean particularly non-enveloped viruses. More specifically, the term "virus" or "viral contaminant(s)" includes so-called highly resistant viruses like the parvoviridae, in particular the porcine parvoviridae, the circoviridae, in particular the porcine circoviridae, and the caliciviridae, in particular the porcine caliciviridae. The porcine parvovirus (PPV) may serve as a generally accepted model or indicator virus for the whole class of highly resistant viruses, in particular highly resistant porcine viruses. Furthermore, the term "virus" or "viral contaminant(s)" in the context of the present disclosure also includes the picornaviridae, in particular the porcine picornaviridae, the reoviridae, in particular the porcine reoviridae, the astroviridae, in particular the porcine astroviridae the adenoviridae, in particular the porcine adenoviridae and the hepeviridae, in particular the porcine hepeviridae.

As used herein, the term "solvent" or "solvents" is intended to mean the amount or proportion of liquid which is present in the pancreatin, either as bound or complexed liquid or as freely available liquid in the pancreatin. Freely available liquid means the liquid present in the pancreatin being heated that is not bound to or not complexed with the pancreatin. Said liquids present in the pancreatin usually comprise water and enzyme friendly organic solvents and mixtures of water with said enzyme friendly organic solvents. Suitable enzyme friendly organic solvents are usually volatile organic solvents like e.g. acetone, chloroform, dichloromethane or straight-chained or branched $C_{1-4}$-alcanols, particularly methanol, ethanol, 1-propanol, 2-propanol, 2-butanol, tert.-butanol or mixtures of said solvents. 2-propanol is preferred as enzyme friendly organic solvent. Typically, the ratio of water to enzyme friendly organic solvent is between 50:1 and 3:1, more typically between 30:1 and 10:1.

Whenever a temperature range, e.g. of from 85° C. to about 100° C., is used, it is intended to mean a temperature anywhere within the expressly mentioned range as well as a temperature profile leading to different temperatures within the expressly mentioned range. The temperature range during the process as disclosed herein can be applied continuously or discontinuously, as long as the overall periods of time within the disclosed temperature ranges are met.

The process described herein comprises heating the pancreatin for a period up to about 48 hours at a temperature of at least 85° C. wherein the total amount of solvents present in the pancreatin is less than about 9% by weight at any point during the heating step.

In one embodiment of such a process, the solvents content of the pancreatin is typically less than about 8%, even more typically less than about 6%, usually less than about 5%, mostly less than about 3.5%, preferably from about 0.1% to about 3.5%, more preferably from about 0.1% to about 3% and even more preferably from about 0.1% to about 1.6% by weight. In other embodiments, the solvent content is less than about 7.5%, 7.0%, 6.5%, 6.0%, 5.5%, 5.0%, 4.5%, 4.0%, 3.5%, 3.0%, 2.5%, 2.0%, 1.5%, 1.0%, or 0.5%.

In one embodiment, the process described herein uses a dispersed pancreatin, in particular a pancreatin powder, with an initial solvents content of about 9% by weight or less, typically between about 2% and about 3.5% by weight. The pancreatin is then heated to the desired process temperature which may be from 85° C. to about 100° C., e.g. 90° C. During the initial heat-up phase, the solvents content in the pancreatin will typically decrease as a function of time and temperature. It is to be understood that the duration of said initial heat-up phase is a function of batch-size and initial batch temperature and therefore may take between approximately 15 minutes and as long as about 10 hours. After the heat-up phase, the pancreatin is heated at a temperature of at least 85° C., usually within the range of 85° C. to about 100° C., e.g. about 90° C., and for the disclosed process time, i.e. for a period of up to about 48 hours, e.g. for a period of 24 hours. When using the process within the parameters disclosed herein (typically under atmospheric pressure), the solvents content reached at the end of the heat-up phase can typically be found to be from about 0.1% to about 1.6% by weight. It can be observed that the solvents content of about 0.1% to about 1.6% by weight reached at the end of the heat-up phase will be relatively constant over the entire range of the preferred process parameters. After termination of the process as described herein, the heated pancreatin may again be exposed to normal ambient conditions (e.g. room temperature and normal moisture conditions). The decrease in viral contaminants in the pancreatin which has been achieved via the process described herein will be maintained under these normal ambient conditions because any viral contaminants as described herein will have been irreversibly deactivated under the process conditions.

In another embodiment, the pancreatin is heated for a period of from about 1 hour to about 36 hours, more preferred for a period of from about 8 hours to about 30 hours, yet more preferred for a period of from about 10 hours to about 24 hours. In an additional embodiment of such process, the dispersed pancreatin is heated for a period of from about 1 hour to about 36 hours, such as, e.g., about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, or 36 hours, and in another embodiment of such process, the dispersed pancreatin is heated for a period of from about 10 hours to about 30 hours.

In another embodiment, the pancreatin is heated at a temperature of from 85° C. to about 100° C., specifically at a temperature of 85° C., 86° C., 87° C., 88° C., 89° C., 90° C., 91° C., 92° C., 93° C., 94° C., 95° C., 96° C., 97° C., 98° C., 99° C., 100° C., or any temperature in the ranges between these given integer temperature values. In a further embodiment of such process, the pancreatin is heated at a temperature of from 85° C. to about 95° C., specifically at a temperature of 85° C., 86° C., 87° C., 88° C., 89° C., 90° C., 91° C., 92° C., 93° C., 94° C., 95° C. or any temperature in the ranges between these given integer temperature values. In other alternatives of this embodiment, the pancreatin is heated at a temperature of from about 90° C. to about 100° C., specifically at a temperature of 90° C., 91° C., 92° C., 93° C., 94° C., 95° C., 96° C., 97° C., 98° C., 99° C., 100° C., or any temperature in the ranges between these given integer temperature values. In a more preferred alternative of this embodiment the pancreatin is heated at a temperature of from about 90° C. to about 95° C., specifically at a temperature of 90° C., 91° C., 92° C., 93° C., 94° C., 95° C. or any temperature in the ranges between these given integer temperature values.

In another embodiment of such a process, the solvents content of the pancreatin is from about 0.1% to about 3.5% by weight and the pancreatin is heated for a period of from about 8 hours to about 30 hours at a temperature of from 85° C. to about 100° C.

In another embodiment of such a process, the solvents content of the pancreatin is from about 0.1% to about 3.0% by weight and the pancreatin is heated for a period of from about 10 hours to about 30 hours at a temperature of from 85° C. to about 95° C.

In another embodiment of such a process, the solvents content of the pancreatin is from about 0.1% to about 1.6% by weight and the pancreatin is heated for a period of from about 10 hours to about 30 hours at a temperature of from 85° C. to about 95° C.

With each single and combined embodiments of such process, the concentration of one or more biological contaminants in the pancreatin is decreased, in particular the concentration of one or more viral contaminants, without substantially affecting the activity of the pancreatin. In one embodiment, the concentration of highly resistant viruses in the pancreatin, more preferably in the concentration of the porcine parvovirus, is decreased.

Also disclosed is a pancreatin obtainable by the process described herein. All provisions made above for the process described herein are also applicable for the pancreatin obtainable by such process.

Another embodiment is directed to a process for manufacturing a pharmaceutical composition comprising pancreatin in accordance with the process described herein wherein such pharmaceutical composition is in a dosage form suitable for oral administration. The oral dosage form can be for immediate and/or modified release, such dosage form can be tablets, microtablets, pellets, micropellets, microspheres, granules, granulates, powders, suspensions, emulsions, dispersions, capsules sachets as well as other dosage forms.

In one embodiment of such process for the manufacturing of a pharmaceutical composition, the pancreatin and/or its dosage form is further coated with a gastric acid resistant coating.

In another embodiment of such process for the manufacture of a pharmaceutical composition, the optionally gastric acid resistant coated pancreatin or its dosage form is further filled into sachets and/or capsules.

Described herein is a pharmaceutical composition comprising
(1) a pharmacologically effective quantity of pancreatin wherein said pancreatin has been heated in the form of a dispersed pancreatin containing one or more solvents, wherein the total amount of solvents present in the pancreatin is less than about 9% by weight at any point during the heating step, to a temperature of at least 85° C.; wherein the titer level of a viral contaminant present in the pancreatin after heating is at least about 1000 times less than the titer level of the viral contaminant present in the pancreatin prior to heating; and
(2) one or more pharmaceutically acceptable excipients.

In an embodiment of such pharmaceutical composition, the pancreatin is present in a dosage form which is suitable for oral administration. The oral dosage form can be for immediate and/or modified release, such dosage form can be tablets, microtablets, pellets, micropellets, microspheres, granules, granulates, powders, suspensions, emulsions, dispersions, capsules, sachets, as well as other dosage forms.

In another embodiment of such pharmaceutical composition the pancreatin and/or the pharmaceutically acceptable excipients are further coated with a gastric acid resistant coating.

Also disclosed is a pharmaceutical composition in the form of a capsule or sachet, the capsule or sachet comprising the pancreatin described herein.

In an embodiment of such pharmaceutical composition, the composition further comprises pharmaceutically acceptable excipients.

In another embodiment of such pharmaceutical composition, the composition is in a dosage form suitable for oral administration. The oral dosage form can be for immediate and/or modified release, such dosage form can be tablets, microtablets, pellets, micropellets, microspheres, granules, granulates, powders, suspensions, emulsions, dispersions, capsules, sachets as well as other known dosage forms.

In another embodiment of such pharmaceutical composition, the pancreatin and/or the pharmaceutically acceptable excipients and/or its dosage form is further coated with a gastric acid resistant coating.

The pharmaceutical compositions described herein may comprise pharmaceutically acceptable excipients. Pharmaceutically acceptable excipients for use in the compositions described above are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, agents, e.g. talcum; buffers, preservatives, antioxidants, lubricants, flavoring and other excipients which are acceptable for use in pharmaceutical formulations.

Generally, a pharmaceutical composition according to the invention may comprise about 0.1% to about 100%, such as, e.g., about 0.1%, 0.2%, 0.3%, 0.4%, 0.5%, 0.6%, 0.7%, 0.8%, 0.9%, 1%, 5%, 10%, 15%, 20%, 25%, 30%, 35%, 40%, 45%, 50%, 55%, 60%, 65%, 70%, 75%, 80%, 85%, 90%, 95%, or 100%, preferably of from about 25% to about 90%, such as, e.g., 25%, 30%, 35%, 40%, 45%, 50%, 55%, 60%, 65%, 70%, 75%, 80%, 85%, or 90%, more preferably from about 50% to about 90%, such as, e.g., 50%, 55%, 60%, 65%, 70%, 75%, 80%, 85%, or 90% by weight, of pancreatin and the remaining proportions, if any, being made up by pharmaceutically acceptable auxiliaries, excipients and/or carriers.

In one embodiment, the pharmaceutical compositions comprise (a) from about 50% to about 90% by weight of pancreatin obtained by the process described herein, and (b) from about 10% to about 50% by weight, of pharmaceutically acceptable excipients, e.g. ethylene glycol polymers, in particular ethylene glycol 2000, 3000, 4000, 6000, 8000 and/or 10000.

In another embodiment, the pharmaceutical compositions comprise (a) from about 55% to about 85% by weight of pancreatin obtained by the process described herein, (b) from about 5% to about 35% by weight of ethylene glycol polymers, (c) from about 1.0% to about 20% by weight of propan-2-ol, and (d) optionally from 0% to about 10% by weight of paraffin. Other compositions comprising pancreatin are e.g. disclosed in EP 0 583 726 and in EP 0 826 375.

The processes described herein may be carried out at any temperature of at least 85° C. which does not result in an unacceptable level of damage to the pancreatin. In accordance with the processes described herein, an "acceptable level" of damage may vary depending upon certain features of the particular processes described herein being employed, such as the nature and characteristics of the particular pancreatin being used, and/or the intended use of the pancreatin being heated, and can be determined empirically by one skilled in the art. An "unacceptable level" of damage would therefore be a level of damage that would preclude the safe and/or effective use of the pancreatin being heated. The particular level of damage to a given pancreatin sample may be determined using any of the methods and techniques known to one skilled in the art.

When used in pharmaceutical compositions, a residual enzyme activity after heating of 50% or more, preferably about 70% or more, more preferably about 85% or more and most preferably about 90% or more, of the original enzyme activity is desirable.

To establish the conditions to minimize the level of enzyme activity decrease, experiments were conducted. In several series of such experiments, the original enzyme activity and the residual enzyme activity of lipase as the leading enzyme were determined before and after heating at certain experimental conditions which are described in detail below.

In a similar series of experiments, the decrease in the concentration of biological contaminants therein was determined. In such experiments, the virus titer values of the highly resistant porcine parvovirus as the leading virus were determined before and after heating under certain experimental conditions which are described in detail below. For each experiment, porcine parvovirus-spiked porcine pancreatin samples were utilized.

The virus titers including standard deviations of the PPV-spiked samples were determined by endpoint titration and subsequent calculation of the half-maximum tissue culture infectious dose (=$TCID_{50}$) according to the Spearman-Kaerber formula as described in the German "Bundesanzeiger" No. 84, May 4, 1994. Therefore, serial one-to-three dilutions of the aliquots were made using cell culture medium and aliquots of each dilution were added using eight-fold replicates in 96-well microtiter plates containing the corresponding target cells. Following an incubation period of six to seven days, the target cells were inspected microscopically for a virus-induced CPE. The virus titers were calculated as mentioned above and these are presented as $\log_{10} TCID_{50}$ per ml with 95% confidence limits. The capacity of the treatment to deactivate or remove viruses was described by means of the logarithmic reduction factors (LRF). This LRF was calculated according to the EC guideline III/8115/89-EN (now replaced by CPMP/BWP/268/95), appendix II as the difference of the viral titers between the hold control samples and the samples which had been exposed to heating.

When used in pharmaceutical compositions, a decrease in the concentration of biological contaminants therein, in particular a decrease in the concentration of viral contaminants, of at least about 3.0, preferably about 3.5, more preferably about 4.0 and most preferably about 4.5 or more log titer reductions is desirable. To comply with authority recommendations on the viral safety of biological products (see e.g. CPMP/BWP/268/95), a process which can provide 4.0 log titer reductions is usually considered robust in terms of virus deactivation and therefore deemed satisfactory.

A log titer reduction thereby indicates the reduction in virus concentration in logarithmic units to the basis 10 (=$\log_{10}$), i.e. a log titer reduction of 3 would comprise a 1000-9999-fold reduction of the viral concentration, while a log titer reduction of 4 would comprise a 10000-99999-fold reduction of the viral concentration. A process for sterilizing pancreatin can be said to be most effective if application of this process results in a satisfactory decrease of even highly resistant viruses in the pancreatin.

To establish the conditions for the most effective log titer reduction, experiments were conducted. Due to technical limitations, it is currently only possible to determine decreases in the concentration of biological contaminants in pancreatin samples of about 4.5 to about 5.0 log titers (detection limit).

In a first series, experiments were conducted in which the lipase activity after heating for specific periods and different but constant temperatures was determined. In the first experiment, the lipase activity after heating for 0, 2, 4, 6, 12, 15, 18, 21, 24 and 30 hours at 80° C. at a solvents content of about 1% was determined. In a second experiment, the lipase activity after heating for 0, 6, 12, 15, 18, 21, 24 and 30 hours at 85° C. at a solvents content of 1% was determined. In a third experiment, the lipase activity after heating for 0, 6, 12, 15, 18, 21, 24 and 30 hours at 90° C. at a solvents content of 1% was determined. In a fourth experiment, the lipase activity after heating for 0, 6, 12, 15, 18, 21, 24 and 30 hours at 95° C. at a solvents content of 1% was determined. In a fifth experiment, the lipase activity after heating for 0, 6, 12, 15, 18, 21, and 24 hours at 100° C. at a solvents content of 1% was determined. The results of this first series of experiments are shown in table 1 and illustrated in FIG. 1.

TABLE 1

Heating of Pancreatin at 80° C., 85° C., 90° C., 95° C. and 100° C. (1% solvents content); the data presented in table 1 are mean values from two incubations; n/a = not applicable; Temp. = Temperature

| Incubation time [h] | Lipase residual activity [%] Temp. | | | | |
| --- | --- | --- | --- | --- | --- |
| | 80° C. | 85° C. | 90° C. | 95° C. | 100° C. |
| 0 | 100.0 | 100.0 | 100.0 | 100.0 | 100.0 |
| 2 | 99.3 | n/a | n/a | n/a | n/a |
| 4 | 99.0 | n/a | n/a | n/a | n/a |
| 6 | 98.8 | 98.9 | 95.0 | 91.1 | 84.0 |
| 12 | 97.7 | 96.2 | 91.7 | 86.1 | 71.4 |
| 15 | 96.5 | 94.7 | 90.6 | 84.2 | 66.3 |
| 18 | 94.6 | 93.5 | 88.6 | 80.1 | 60.3 |
| 21 | 93.6 | 93.5 | 87.0 | 77.8 | 56.0 |
| 24 | 92.5 | 92.1 | 85.8 | 77.8 | 52.8 |
| 30 | 91.3 | 90.7 | 83.7 | 74.8 | n/a |

As can be seen from table 1 and from FIG. 1 for a constant solvents content of 1%, the lipase activity decreases as incubation time increases at a given temperature. Furthermore, the lipase activity declines to a greater extent at high temperatures at a given incubation time. When used in pharmaceutical compositions, it follows that heating conducted for a period of up to and including 30 hours at temperatures up to and including 95° C. provide pancreatin having acceptable residual enzyme activity at a solvents content of 1%. When used in pharmaceutical compositions, it follows further that heating conducted for a period of up to and including 24 hours at temperatures up to and including 100° C. provide pancreatin having acceptable residual enzyme activity at a solvents content of 1%.

In a second series, two experiments were conducted in which the lipase activity at a solvents content of 3% was determined after heating. In the first experiment, the lipase activity after heating for 0, 2, 4, 6, 8, 15, 24 and 48 hours at 90° C. and 95° C. at a solvents content of 3% was determined. The results of this second series of experiments are shown in table 2 and illustrated in FIG. 2.

TABLE 2

Heating of Pancreatin at 90° C. and 95° C. (3% solvents content).

| Incubation | Lipase residual activity [%] Temperature | |
|---|---|---|
| time [h] | 90° C. | 95° C. |
| 0 | 100.0 | 100.0 |
| 2 | 94.1 | 95.1 |
| 4 | 91.0 | 90.2 |
| 8 | 86.8 | 81.4 |
| 15 | 84.0 | 66.0 |
| 24 | 71.4 | 54.1 |
| 48 | 53.5 | 31.3 |

As can be seen from table 2 and from FIG. 2 for a constant solvents content of 3%, the lipase activity decreases as incubation time increases at a given temperature. Furthermore, the lipase activity declines to a greater extent at high temperatures at a given incubation time. When used in pharmaceutical compositions, it follows that heating conducted for a period of up to and including 48 hours at temperatures up to and including 90° C. provide pancreatin having acceptable residual enzyme activity at a solvents content of 3%. When used in pharmaceutical compositions, it follows further that heating conducted for a period of up to and including 24 hours at temperatures up to and including 95° C. provide pancreatin having acceptable residual enzyme activity at a solvents content of 3%.

In a third series of experiments, the lipase activity was determined after heating for 0.5, 1.0 and 3.0 hours at 80° C. at different but constant solvents contents of 3%, 6%, 9% and 12%, respectively. The results of these experiments are shown in table 3 and are illustrated in FIG. 3.

TABLE 3

Heating Pancreatin at 80° C. with a solvents content of 3%, 6%, 9% and 12%, respectively.

| Incubation | Lipase residual activity [%] Solvents Content | | | |
|---|---|---|---|---|
| time [h] | 3% | 6% | 9% | 12% |
| 0 | 100.0 | 100.0 | 100.0 | 100.0 |
| 0.5 | 101.2 | 92.8 | 63.0 | 37.8 |
| 1.0 | 100.5 | 88.2 | 50.7 | 23.9 |
| 3.0 | 100.1 | 73.5 | 33.5 | 12.8 |

It can be seen from table 3 and from FIG. 3 for a constant temperature but different solvents contents of 3%, 6%, 9% and 12%, respectively, the lipase activity decreases as incubation time increases at 80° C. Furthermore, the lipase activity declines to a greater extent at high solvents contents at a given incubation time. When used in pharmaceutical compositions, it follows that heating conducted for a period of up to and including 3 hours at a temperature of 80° C. provide pancreatin having acceptable residual enzyme activity at a solvents content of 6%. When used in pharmaceutical compositions, it follows further that heating conducted for a period of up to and including 1 hour at a temperature of 80° C. provide pancreatin having acceptable residual enzyme activity at a solvents content of 9%.

This series of experiments demonstrates that enzymes are sensitive to extended periods of heat and sensitive to high solvents contents. Their high original activity is maintained if heating occurs under controlled conditions, i.e., over short periods, and/or at low temperatures, and/or at low solvents contents. In an embodiment, the high original enzyme activity is maintained if the enzymes are heated at low temperatures and at low solvents contents over a short period of time.

To evaluate the reduction in the porcine parvovirus, the $\log_{10}$ TCID$_{50}$ after heating for 6, 12, 15, 18, 21, 24 and 30 hours at 80° C., 85° C., 90° C., 95° C. and 100° C. were determined at a constant solvent contents of 1%. The results of these experiments are shown in table 4. In table 4 and the following tables, titers which are indicated as "smaller than" ($\leq$) express the detection limit.

TABLE 4

Heating of PPV-spiked pancreatin at 80° C., 85° C., 90° C., 95° C. and 100° C. with a solvents content of 1%; n/a = not applicable; Temp. = Temperature; h = hours; LTR = Log Titer Reduction.

| Incubation | the $109_{10}$ TCID$_{50}$ of PPV-spiked Pancreatin Incubation Temp.: | | | | |
|---|---|---|---|---|---|
| Time [h] | 80° C. | 85° C. | 90° C. | 95° C. | 100° C. |
| 0 h | 7.2 | 7.2 | 7.8 | 7.8 | 7.8 |
| 6 h | 6.9 | 6.0 | 5.5 | 4.7 | n/a |
| 12 h | 5.6 | ≤5.1 | 4.0 | 3.9 | ≤3.8 |
| 15 h | 5.8 | ≤4.1 | ≤3.8 | ≤3.8 | n/a |
| 18 h | ≤5.0 | ≤4.0 | ≤3.8 | ≤3.8 | n/a |
| 21 h | ≤4.8 | ≤3.9 | ≤3.8 | ≤3.8 | n/a |
| 24 h | ≤4.6 | ≤3.9 | ≤3.8 | ≤3.8 | ≤3.8 |
| 30 h | ≤4.2 | ≤3.8 | ≤3.8 | ≤3.8 | n/a |
| 18 h hold | 7.9 | 7.5 | 7.7 | 7.8 | 7.8 (24 h hold) |
| 30 h hold | 7.5 | 7.5 | 7.4 | 7.3 | n/a |
| LTR (18 h hold versus 18 h x° C.) | ≥2.9 | ≥3.5 | 3.9 | 4.0 | n/a |
| LTR (30 h hold versus 30 h at x° C.) | ≥3.3 | ≥3.7 | 3.6 | 3.5 | 4.0 (24 h hold vs. 24 h at 100° C.) |

Additional pancreatin powder batches 2 to 4 were prepared and processed at 85° C. as described above in table 4 and below in Example 13. To evaluate the reduction in the porcine parvovirus, again the $\log_{10}$ TCID$_{50}$ after heating for 6, 12, 15, 18, 21, 24 and 30 hours at 85° C. were determined at a constant solvent content of 1%. The results of these additional experiments are shown in table 4a.

TABLE 4a

Heating of 3 different batches of PPV-spiked pancreatin at 85° C. with a solvents content of 1%. Values given as "±" denominate the 95% confidence intervals. "*" means that no infectious virus could be detected; Temp. = Temperature; h = hours; LTR = Log Titer Reduction.

| Incubation Time | the $\log_{10}$ TCID$_{50}$ of PPV-spiked Pancreatin/85° C. Batch No. | | |
|---|---|---|---|
| [h]/Temp. | 2 | 3 | 4 |
| 0 h | 7.5 ± 0.2 | 7.5 ± 0.2 | 7.2 ± 0.3 |
| 6 h | 5.9 ± 0.3 | 5.6 ± 0.2 | 5.9 ± 0.2 |
| 12 h | 4.9 ± 0.3 | ≤4.6 ± 0.4 | 4.8 ± 0.3 |
| 15 h | ≤4.3 ± 0.3 | ≤4.3 ± 0.3 | ≤4.4 ± 0.3 |
| 18 h | ≤4.1 ± 0.3 | ≤3.8 ± 0.2 | ≤4.2 ± 0.1 |
| 21 h | ≤3.9 ± 0.2 | ≤3.8 ± 0.2 | ≤3.9 ± 0.2 |
| 24 h | ≤3.7 ± 0.1 | 3.7* | ≤3.8 ± 0.1 |
| 30 h | ≤3.7 ± 0.1 | ≤3.7 ± 0.1 | 3.8* |
| 18 h hold | 7.7 ± 0.2 | 7.7 ± 0.3 | 7.7 ± 0.3 |
| 30 h hold | 7.7 ± 0.3 | 7.4 ± 0.3 | 7.6 ± 0.3 |

TABLE 4a-continued

Heating of 3 different batches of PPV-spiked pancreatin at 85° C. with a solvents content of 1%. Values given as "±" denominate the 95% confidence intervals. "*" means that no infectious virus could be detected; Temp. = Temperature; h = hours; LTR = Log Titer Reduction.

| Incubation Time [h]/Temp. | the $\log_{10}$ TCID$_{50}$ of PPV-spiked Pancreatin/85° C. Batch No. | | |
|---|---|---|---|
| | 2 | 3 | 4 |
| LTR (18 h hold versus 18 h at 85° C.) | ≥3.6 ± 0.4 | ≥3.9 ± 0.4 | ≥3.5 ± 0.3 |
| LTR (30 h hold versus 30 h at 85° C.) | ≥4.0 ± 0.3 | ≥3.7 ± 0.3 | ≥3.8 ± 0.3 |

Table 5 shows the log titer reduction in comparison to the beginning of the experiment. FIG. 4 illustrates the log titer reduction of PPV-spiked pancreatin after heating at 80° C., 85° C., 90° C., 95° C. and 100° C. with a solvents content of 1%.

TABLE 5

Log Titer Reduction after heating of PPV-spiked pancreatin at 80° C., 85° C., 90° C., 95° C. and 100° C. with a solvents content of 1%; n/a = not applicable; Temp. = Temperature.

| Incubation time [h] | Log Titer Reduction of porcine parvovirus Temp. | | | | |
|---|---|---|---|---|---|
| | 80° C. | 85° C. | 90° C. | 95° C. | 100° C. |
| 0 | 0.0 | 0.0 | 0.0 | 0.0 | 0.0 |
| 6 | 0.3 | 1.2 | 2.3 | 3.1 | n/a |
| 12 | 1.6 | ≥2.1 | 3.8 | 3.9 | ≥4.0 |
| 15 | 1.4 | ≥3.1 | ≥4.0 | ≥4.0 | n/a |
| 18 | ≥2.2 | ≥3.2 | ≥4.0 | ≥4.0 | n/a |
| 21 | ≥2.4 | ≥3.3 | ≥4.0 | ≥4.0 | n/a |
| 24 | ≥2.6 | ≥3.3 | ≥4.0 | ≥4.0 | 4.0 |
| 30 | ≥3.0 | ≥3.4 | ≥4.0 | ≥4.0 | n/a |

As can be seen from tables 4 and 5 as well as from FIG. 4 for a constant solvents content of 1%, the log titer reduction increases as incubation time increases at a given temperature. Furthermore, the log titer reduction declines to a greater extent as temperature increases. When used in pharmaceutical compositions, it follows that heating conducted for a period of up to and including 30 hours at a temperature of 80° C. provide pancreatin having an acceptable decrease in the concentration of biological contaminants therein at a solvents content of 1%. Experiments conducted for a period of 12 hours and at a temperature of 90° C. provide pancreatin having a decrease in the concentration of biological contaminants therein at a solvents content of 1%. Experiments conducted for a period of 15 hours and at a temperature of 90° C. provide pancreatin having an even larger decrease in the concentration of biological contaminants therein at a solvents content of 1%.

From table 4a it can be seen that the authorities' recommendations on the viral safety of biological products (see e.g. CPMP/BWP/268/95) can be met when the parameters as given in table 4a are applied, i.e. 4.0 log titer reductions may be reached at process temperatures of 85° C. (see e.g. batch 2, LTR after 30 hours). Similar experiments with additional batches processed at 80° C. showed that the authorities' recommendations on the viral safety of biological products could not be met, i.e. that 4.0 log titer reductions could not be reached at process temperatures of 80° C.

In another series of experiments, the $\log_{10}$ TCID$_{50}$ after heating for up to 12 hours at a constant temperature and at different but constant solvents content of 1% and 3% respectively was determined. The results of these experiments are shown in table 6.

TABLE 6

Heating of PPV-spiked pancreatin at 90° C. and 95° C. with a solvent content of 1% and 3%, respectively.

| Incubation time [h] | The $\log_{10}$ TCID$_{50}$ of PPV-spiked Pancreatin Temperature | | | |
|---|---|---|---|---|
| | 90° C., 1% solvents content | 90° C., 3% solvents content | 95° C., 1% solvents content | 95° C., 3% solvents content |
| 0 | 8.2 | 8.2 | 8.2 | 8.2 |
| 3 | 6.8 | 6.2 | 6.4 | 6.1 |
| 6 | 5.9 | 5.8 | 6.1 | 5.1 |
| 12 | 5.0 | 4.9 | 4.6 | 5.0 |

Table 7 shows the log titer reduction (for the results as presented in table 5) in porcine parvovirus relative to the initial amount. FIG. 5 illustrates the log titer reduction of PPV-spiked pancreatin after heating at 90° C. and 95° C. with a solvents content of 1% and 3%, respectively. The experiments leading to the results as presented in tables 6 and 7 were performed under slightly different conditions compared with the experiments leading to the results as presented in table 5.

TABLE 7

Log Titer reduction after heating of PPV-spiked pancreatin at 90° C. and 95° C. with a solvents content of 1% and 3%, respectively.

| Incubation time [h] | Log Titer Reduction of porcine parvovirus (PPV) Temperature | | | |
|---|---|---|---|---|
| | 90° C., 1% solvents content | 90° C., 3% solvents content | 95° C., 1% solvents content | 95° C., 3% solvents content |
| 0 | 0.0 | 0.0 | 0.0 | 0.0 |
| 3 | 1.4 | 2.0 | 1.8 | 2.1 |
| 6 | 2.3 | 2.4 | 2.1 | 3.1 |
| 12 | 3.2 | 3.3 | 3.6 | 3.2 |

It can be seen from tables 6 and 7 as well as from FIG. 5 for a constant solvents content of 1% and 3% respectively, that the log titer reduction increases as incubation time increases at a given temperature. Furthermore, the log titer reduction increases to a greater extent at 3% solvents contents as opposed to 1%. For-use in pharmaceutical compositions, it follows that heating for a period of at least 6 hours at a temperature of 95° C. will provide pancreatin having an acceptable decrease in the concentration of biological contaminants therein at a solvents content of 3%. For use in pharmaceutical compositions, it follows that heating conducted for a period of 12 hours at a temperature of 90° C. provide pancreatin having an acceptable decrease in the concentration of biological contaminants therein at a solvents content of 1% or 3%, respectively.

This series of experiments demonstrates that the concentration of porcine parvovirus can be effectively reduced by heating under the conditions set forth above. It can be concluded from the above experiments that the reduction is more effective at high temperatures and/or over a long period of time and/or at higher solvents content. In an embodiment, the concentration of the porcine parvovirus can be effectively reduced if the virus is heated at a suitably elevated temperature and solvents contents over a sufficient period of time.

The results obtained for the decrease in the concentration of porcine parvovirus are in contrast to what has been demonstrated for enzymes. Hence, the skilled person in the art is faced with the challenge of designing a process of sterilizing pancreatin in such a way that a high level of activity of the different digestive enzymes is maintained while at the same time the concentration of one or more biological contaminants, in particular of viruses, therein is reduced to an acceptable level.

From the above experiments it can be seen that the concentration of porcine parvovirus in pancreatin under experimental conditions is reduced while the lipase activity level remains acceptable for the use in pharmaceutical compositions. These experimental conditions can be summarized as follows:

Heating for a period up to 48 hours at a temperature of at least 85° C. at a solvent content of less than about 9% by weight.

The steps of adjusting the solvents content and heating may occur at any pressure which is not deleterious to the pancreatin being heated. Generally, the disclosed processes are conducted at atmospheric, reduced or elevated pressure. Suitable pressures can be determined empirically by one skilled in the art. In an embodiment, the processes are conducted at atmospheric or reduced pressure. In another embodiment, the processes are conducted at atmospheric pressure. According to another embodiment, the processes described herein are conducted under vacuum while being sterilized.

Similarly, according to the processes described herein, heating may occur under any atmosphere that is not deleterious to the pancreatin being treated. Typically, the processes described herein are conducted in standard atmosphere. According to one embodiment, the disclosed processes are conducted in a low oxygen atmosphere or an inert atmosphere. When an inert atmosphere is employed, the atmosphere is preferably composed of nitrogen or a noble gas, such as helium or argon, more preferably a higher molecular weight noble gas, and most preferably argon. It will be appreciated that the combination of one or more of the features described herein may be employed to further minimize undesirable effects upon the processes described herein, while maintaining adequate effectiveness of the processes on the biological contaminant(s).

The solvents content of pancreatin may be reduced by any of the methods and techniques known to those skilled in the art for reducing solvent from a preparation of one or more digestive enzymes without producing an unacceptable level of damage to the preparation. Such methods include, but are not limited to, evaporation, concentration, centrifugal concentration, vitrification, addition of solute, lyophilization (with or without the prior addition of ascorbate) and spray-drying.

A preferred method for reducing the solvents content of pancreatin is concentration, which may be accomplished by any of the methods and techniques known to those skilled in the art. Concentration may be achieved either by controlled heating of the preparation and subsequent evaporation of the unwanted solvent or by evaporation via reduced pressure. Also a combination of these two methods under mild conditions, evaporation at low temperature under reduced pressure, may be applied in order to achieve the desired solvents content. Regardless of the method used, the resulting preparation will then have the desired solvents content.

The processes described herein may be conducted at any scale, at laboratory scale with preparations having a mass from 1 g to 1000 g; at pilot plant scale with preparations having a mass from 1 kg to 50 kg and a production scale with preparations having a mass from at least 100 kg, preferably from 200 kg to 1500 kg.

EXAMPLES

The following examples are illustrative, and not meant to limit the claimed invention. Other suitable modifications and adaptations are of the variety normally encountered by those skilled in the art and are fully within the spirit and scope of the claimed invention.

Determination of Enzymatic Activity

The determination of the lipase activity was performed according to a Solvay testing method which is based on the monograph of pancreas powder in Ph. Eur. (Pancreas Powder, European Pharmacopoeia 5.0, 2179-2182; 01/2005: 0350).

Determination of Solvent Content

The solvents contents related as water referenced herein refer to levels determined by the FDA approved, modified Karl Fischer method (Meyer and Boyd, Analytical Chem., 31:215-219, 1959; May, et al., J. Biol. Standardization, 10:249-259, 1982; Centers for Biologics Evaluation and Research, FDA, Docket No. 89D-0140, 83-93; 1990). Quantitation of the contents of other solvents may be determined by means known to those of skill in the art, depending on which solvent is employed. Further suitable means for determining solvent contents in the pancreatin during or after the process disclosed herein, which are also included in the present disclosure, are e.g. thermogravimetric methods (including infrared drying and microwave drying), spectrometric methods (including infrared spectroscopy, microwave spectroscopy and nuclear magnetic resonance spectroscopy), conductometry, decametry, or thermal conduction. Usually, the preferred method for determining the solvents contents in pancreatin is a thermogravimetric method (e.g. determination of "loss on drying"), since this method would cover all liquids which may be present in the pancreatin, comprising e.g. water and enzyme friendly organic solvents like isopropanol. Thermogravimetric methods are in particular suited for measuring solvents contents of about 9%-3.5% by weight in the pancreatin. Where lower solvents contents are to be determined in the pancreatin, e.g. solvents contents below about 3.5%, more typically of less than 3%, even more typically of less than 1.6% by weight, the proportion of water present in the solvents content of pancreatin will typically outweigh the proportion of enzyme friendly organic solvent present in the pancreatin. It may therefore be advantageous to measure solvents contents below about 3.5%, more typically of less than 3%, even more typically of less than 1.6% by weight by using the more sensitive Karl Fischer method or a modification thereof. For technical batch sizes and continuous measuring, infrared spectroscopic determination of the solvent contents is advantageous, in particular where solvents contents below about 3.5%, more typically of less than 3%, even more typically of less than 1.6% by weight are to be measures, e.g. in the steady state of the heating process after the preheating. Preferred are near infrared spectroscopy determination methods (NIR) which are known to those skilled in the art. The infrared spectoscopic methods will typically need to be standardized against a reference method which can be the Karl-Fischer water titration method or a modification thereof. For the reasons as outlined above, the most preferred method of measuring the total solvents content in a pancreatin is a combination of a thermogravimetric method (i.e. determining the loss on drying in the pancreatin, in particular for a pancreatin with a higher solvents content) with a Karl Fischer method or a modification thereof (i.e. determining the remaining water content in the pancreatin, in particular for a pancreatin with a lower solvents content.

Determination of Porcine Parvovirus Reduction

The virus titers within the treated samples were determined by virus endpoint titration and the $TCID_{50}$ was calculated according to the Spearman-Kaerber formula as described in the Bundesanzeiger No. 84, May 4, 1994. In order to circumvent incompatibility of the pancreatin with the detector Pk-13-cells (porcine kidney), the test material was diluted by 3 log titers (e.g. 1:2000) prior to titration in each case. The ability of the treatment to deactivate or remove viruses was described by means of the logarithmic reduction factors. In order to be able to estimate the reduction of virus titers independently from obligatory decrease of infectivity during the incubation period, which to some extent may result from the properties of the test material itself, hold samples were taken. The logarithmic titer reduction (LTR) of the samples was calculated as the difference between the virus titer ($\log_{10} TCID_{50}/ml$) of the hold sample and the final point sample according to the EC guideline III/8115/89-EN, appendix II (now replaced by CPMP/BWP/268/95).

Heating

For laboratory scale, heating was performed in a drying oven (e.g. from company Memmert, ULE 400) or rotary evaporator (e.g. from company Büchi, R-144) with a water bath (e.g. Büchi B-480). In the pilot plant scale, a vacuum dryer (company: Hosokawa, Vrieco-Nauta®, volume 120 L) was used. In the production scale, a vacuum dryer (company: Hosokawa, Vrieco-Nauta®, volume 4000 L) was used.

Preparation of Standardized Pancreatin Powder 50 kg to 1000 kg of moist pancreatin (initial solvents content 40-50%) was dried in a vacuum dryer with continuous stirring. The temperature was increased stepwise from 60° C. to 95° C. Drying was then carried out at a temperature of at least 70° C. until a solvents content of <3.5% is reached. To obtain pancreatin powder samples of solvent contents of 6%, 9% or 12% by weight, respectively, samples may be taken at appropriate earlier points during the drying process in a known manner.

a) Further steps for the preparation of standardized pancreatin powder on a laboratory scale include heating at the desired temperature until a solvents content of 1%, or 3% by weight, respectively, was reached in accordance with the starting requirements of the experiments described below (examples 1 to 11 below).

For an alternative preparation of standardized pancreatin powder having a solvents content of 6%, 9% or 12% by weight, respectively, an appropriate amount of a solvent e.g., water, propan-2-ol or mixtures thereof, may be added to a pancreatin powder with a solvents content of 3.5% by weight, and the obtained moistened pancreatin sample may be homogenized as needed so that a sample with the desired solvents content is obtained.

b) Further steps for the preparation of standardized pancreatin powder on a pilot plant and production scale include heating at the desired temperature until a solvents content of 1% by weight and a temperature of from 80° C. to 100° C. was reached in accordance with the starting requirements of the experiments described below (examples 1 to 11 below).

Further Processing of Pancreatin for Porcine Parvovirus Studies:

According to generally accepted principles in the scientific and pharmacological communities, pancreatin was spiked with added porcine parvovirus in order to establish proof of principle. The spiking was conducted according to the guideline CPMP/BWP/268/95.

After performing the standard drying of the production process (see above) on pancreatin, the pancreatin powder was cooled down and re-suspended in water (resulting in a 40% suspension in order to obtain a homogeneous distribution of the spiked virus within the pancreatin powder). The pancreatin was then spiked with a highly concentrated porcine parvovirus suspension in cell culture medium in a ratio 9:1 (pancreatin suspension:virus suspension). The resulting suspension was then lyophilized and subsequently heated at a temperature of from 80° C. to 100° C. until a solvents content of 1% and 3% by weight, respectively, was reached in accordance with the starting requirements of the experiments described below (examples 12 to 20 as below).

Example 1

48 kg of standardized pancreatin with a solvents content of 1% was subsequently heated at 80° C. for a period of 30 hours. The lipase activity was determined after 0, 2, 4, 6, 12, 15, 18, 21, 24 and 30 hours. The results of this experiment are shown in table 1 and in FIG. 1.

Example 2

48 kg of standardized pancreatin with a solvents content of 1% was subsequently heated at 85° C. for a period of 30 hours. The lipase activity was determined after 0, 6, 12, 15, 18, 21, 24 and 30 hours. The results of this experiment are shown in table 1 and in FIG. 1.

Example 3

48 kg of standardized pancreatin with a solvents content of 1% was subsequently heated at 90° C. for a period of 30 hours. The lipase activity was determined after 0, 6, 12, 15, 18, 21, 24 and 30 hours. The results of this experiment are shown in table 1 and in FIG. 1.

Example 4

48 kg of standardized pancreatin with a solvents content of 1% was subsequently heated at 95° C. for a period of 30 hours. The lipase activity was determined after 0, 6, 12, 15, 18, 21, 24 and 30 hours. The results of this experiment are shown in table 1 and in FIG. 1.

Example 5

48 kg of standardized pancreatin with a solvents content of 1% was subsequently heated at 100° C. for a period of 30 hours. The lipase activity was determined after 0, 6, 12, 15, 18, 21 and 24 hours. The results of this experiment are shown in table 1 and in FIG. 1.

Example 6

1.5 g of standardized pancreatin with a solvents content of 3% was subsequently heated at 90° C. for a period of 48 hours. The lipase activity was determined after 0, 2, 4, 8, 6, 15, 24 and 48 hours. The results of this experiment are shown in table 2 and in FIG. 2.

Example 7

1.5 g of standardized pancreatin with a solvents content of 3% was subsequently heated at 95° C. for a period of 48 hours. The lipase activity was determined after 0, 2, 4, 8, 6, 15, 24 and 48 hours. The results of this experiment are shown in table 2 and in FIG. 2.

Example 8

1.5 g of standardized pancreatin with a solvents content of 3% was subsequently heated at 80° C. for a period of 3.0 hours. The lipase activity was determined after 0.5, 1.0 and 3.0 hours. The results of this experiment are shown in table 3 and in FIG. 3.

Example 9

1.5 g of standardized pancreatin with a solvents content of 6% was subsequently heated at 80° C. for a period of 3.0 hours. The lipase activity was determined after 0.5, 1.0 and 3.0 hours. The results of this experiment are shown in table 3 and in FIG. 3.

Example 10

1.5 g of standardized pancreatin with a solvents content of 9% was subsequently heated at 80° C. for a period of 3.0 hours. The lipase activity was determined after 0.5, 1.0 and 3.0 hours. The results of this experiment are shown in table 3 and in FIG. 3.

Example 11

1.5 g of standardized pancreatin with a solvents content of 12% was subsequently heated at 80° C. for a period of 3.0 hours. The lipase activity was determined after 0.5, 1.0 and 3.0 hours. The results of this experiment are shown in table 3 and in FIG. 3.

Example 12

1.5 g of porcine parvovirus-spiked pancreatin with a solvents content of 1% was subsequently heated at 80° C. for a period of 30 hours. The virus concentration was determined after 6, 12, 15, 18, 21, 24 and 30 hours. The results of this experiment are shown in tables 4 and 5 as well as in FIG. 4.

Example 13

1.5 g of porcine parvovirus-spiked pancreatin with a solvents content of 1% was subsequently heated at 85° C. for a period of 30 hours. The virus concentration was determined after 6, 12, 15, 18, 21, 24 and 30 hours. The results of this experiment are shown in tables 4, 4a, and 5 as well as in FIG. 4.

Example 14

1.5 g of porcine parvovirus-spiked pancreatin with a solvents content of 1% was subsequently heated at 90° C. for a period of 30 hours. The virus concentration was determined after 6, 12, 15, 18, 21, 24 and 30 hours. The results of this experiment are shown in tables 4 and 5 as well as in FIG. 4.

Example 15

1.5 g of porcine parvovirus-spiked pancreatin with a solvents content of 1% was subsequently heated at 95° C. for a period of 30 hours. The virus concentration was determined after 6, 12, 15, 18, 21, 24 and 30 hours. The results of this experiment are shown in tables 4 and 5 as well as in FIG. 4.

Example 16

1.5 g of porcine parvovirus-spiked pancreatin with a solvents content of 1% was subsequently heated at 100° C. for a period of 30 hours. The virus concentration was determined after 6, 12, 15, 18, 21, 24 and 30 hours. The results of this experiment are shown in tables 4 and 5 as well as in FIG. 4.

Example 17

1.5 g of porcine parvovirus-spiked pancreatin with a solvents content of 1% was subsequently heated at 90° C. for a period of 12 hours. The virus concentration was determined after 3, 6 and 12 hours. The results of this experiment are shown in tables 6 and 7 as well as in FIG. 5.

Example 18

1.5 g of porcine parvovirus-spiked pancreatin with a solvents content of 3% was subsequently heated at 90° C. for a period of 12 hours. The virus concentration was determined after 3, 6 and 12 hours. The results of this experiment are shown in tables 6 and 7 as well as in FIG. 5.

Example 19

1.5 g of porcine parvovirus-spiked pancreatin with a solvents content of 1% was subsequently heated at 95° C. for a period of 12 hours. The virus concentration was determined after 3, 6 and 12 hours. The results of this experiment are shown in tables 6 and 7 as well as in FIG. 5.

Example 20

1.5 g of porcine parvovirus-spiked pancreatin with a solvents content of 3% was subsequently heated at 95° C. for a period of 12 hours. The virus concentration was determined after 3, 6 and 12 hours. The results of this experiment are shown in tables 6 and 7 as well as in FIG. 5.

Example 21

Pharmaceutical Composition Comprising Pancreatin

A composition comprising the pancreatin obtained by the process described herein is obtained as follows: 10 kg of pancreatin obtained by the process of example 2 is mixed with 2.5 kg of ethylene glycol 4000 and 1.5 kg of propan-2-ol to give a mixture which was then extruded in a known manner in an extruding press. Pancreatin micropellets are prepared as disclosed in EP 0 583 726 and can be further packed into capsules or sachets.

Example 22

Pancreatin Micropellets Coated with a Gastric Acid Resistant Coating

The pancreatin micropellet cores obtained by example 21 can be provided with a gastric acid resistant coating. For example, the pancreatin micropellet cores can be coated with gastric-juice-resistant film-forming agents such as, e.g., hydroxypropylmethylcellulose acetate succinate (=HPMCAS), hydroxypropylmethylcellulose phthalate (=HPMCP), cellulose acetate phthalate (=CAP) or polyvinyl acetate phthalate (=PVAP). Copolymers known as film-forming agents such as, for example, methacrylic acid/methyl methacrylate copolymers or methacrylic acid/ethyl acrylate copolymers, can also be used. The film-forming agents can be applied to the pancreatin micropellet cores using various film-coating apparatus, e.g. coaters, in the customary use forms, e.g. as organic solutions or organic or aqueous dispersions, optionally with addition of a conventional plasticizer. The resulting gastric acid-resistant film-coated pancreatin micropellets are distinguished by a high bulk density, for example in the range from 0.6 g/ml to 0.85 g/ml, which makes it possible to increase the filling weight per capsule and thus the active compound content of each capsule. Further experimental details on the process for preparing the gastric acid-resistant film-coated pancreatin micropellets are disclosed in EP 0 583 726.

All references, including publications, patent applications, and patents, cited herein are hereby incorporated by reference to the same extent as if each reference were individually and specifically indicated to be incorporated by reference and were set forth in its entirety herein.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the particular subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it there individually recited herein.

Use of the phrase 'the invention' or 'the present invention' is not meant to limit the claims in any manner and no conclusion should be drawn that any description or argument associated with a particular use of the phrase 'the invention' or 'the present invention' applies to each and every claim. The use of the phrase 'the invention' or 'the present invention' has been used solely for linguistic or grammatical convenience and not to effect a limitation of any nature on any of the claims.

Alternative embodiments of the claimed invention are described herein, including the best mode known to the inventors for carrying out the claimed invention. Of these, variations of the disclosed embodiments will become apparent to those of ordinary skill in the art upon reading the foregoing disclosure. The inventors expect skilled artisans to employ such variations as appropriate, and the inventors intend for the claimed invention to be practiced otherwise than as specifically described herein. Accordingly, the claimed invention includes all modifications and equivalents of the subject matter recited in the claims appended hereto as permitted by applicable law. Moreover, any combination of the above-described elements in all possible variations thereof is encompassed by the claimed invention unless otherwise indicated herein or otherwise clearly contradicted by context.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

The use of the terms "a" and "an" and "the" and similar referents in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the claimed invention.

We claim:

1. A process for the manufacture of pancreatin, comprising the steps of:
   heating a dispersed form of pancreatin containing one or more solvents at:
   (a) a temperature from 80° C. to 90° C. for a period of between about 30 hours and about 48 hours,
   (b) a temperature from 85° C. to 95° C. for a period of between about 12 hours and about 30 hours, or
   (c) a temperature from 95° C. to 100° C. for a period of between about 6 hours and about 24 hours;
   wherein the total amount of the one or more solvents is equal to or less than about 1% by weight at any point during the heating step; and wherein the titer level of any porcine parvovirus present in the dispersed pancreatin after heating is at least about 1000 times less than the titer level of said porcine parvovirus present in the dispersed pancreatin prior to heating; and wherein pancreatin lipase activity after heating is at least about 50% of the lipase activity prior to heating.

2. The process of claim 1 wherein the pancreatin lipase activity after heating is at least about 70% of the lipase activity prior to heating.

3. The process of claim 1 wherein the pancreatin lipase activity after heating is at least about 90% of the lipase activity prior to heating.

4. The process of claim 1 wherein the heating of the pancreatin is at a temperature from 80° C. to 90° C. for a period of between about 30 hours and about 48 hours.

5. The process of claim 1 wherein the heating of the pancreatin is at a temperature from 85° C. to 95° C. for a period of between about 12 hours and about 30 hours.

6. The process of claim 1 wherein the heating of the pancreatin is at a temperature from 95° C. to 100° C. for a period of between about 6 hours and about 24 hours.

7. The process of claim 1 wherein the titer level of the porcine parvovirus present in the pancreatin after heating is at least about 5000 times less than the titer level of the porcine parvovirus present in the pancreatin prior to heating.

8. The process of claim 1 wherein the titer level of the porcine parvovirus present in the pancreatin after heating is at least about 10,000 times less than the titer level of the porcine parvovirus present in the pancreatin prior to heating.

9. A process for the manufacture of pancreatin, comprising
(1) heating a dispersed form of pancreatin containing one or more solvents at:
(a) a temperature from 80° C. to 90° C. for a period of between about 30 hours and about 48 hours,
(b) a temperature from 85° C. to 90° C. for a period of between about 15 hours and about 30 hours,
(c) a temperature from 90° C. to 100° C. for a period of between about 12 hours and about 24 hours, or
(d) a temperature from 95° C. to 100° C. for a period of between about 6 hours and about 18 hours, and
(2) obtaining a total solvents content in the dispersed form of pancreatin of equal to or less than about 3.5% by weight at any point during said heating step;
wherein the titer level of any porcine parvovirus present in the dispersed pancreatin after heating is at least about 1000 times less than the titer level of said porcine parvovirus present in the dispersed pancreatin prior to heating; and
wherein lipase activity of the dispersed pancreatin after heating is at least about 50% of lipase activity of the dispersed pancreatin prior to heating.

10. The process of claim 9 wherein the heating step is performed continuously.

11. The process of claim 9 wherein the heating step is performed discontinuously.

12. The process of claim 9 wherein the solvents content in the pancreatin is determined by a Karl Fischer water titration method or by an infrared spectroscopy method.

13. The process of claim 9 wherein lipase activity of the dispersed pancreatin after heating is at least about 70% of lipase activity of the dispersed pancreatin prior to heating.

14. A process for the manufacture of pancreatin, comprising the steps of:
heating a dispersed form of pancreatin having a total solvent content equal to or less than 3.5% at:
(a) a temperature from 80° C. to 90° C. for a period of between about 30 hours and about 48 hours,
(b) a temperature from 85° C. to 90° C. for a period of between about 12 hours and about 30 hours, or
(c) a temperature from 90° C. to 95° C. for a period of between about 6 hours and about 12 hours;
wherein the titer level of any porcine parvovirus present in the dispersed pancreatin after heating is at least about 1000 times less than the titer level of said porcine parvovirus present in the dispersed pancreatin prior to heating; and
wherein lipase activity of the dispersed pancreatin after heating is at least about 70% of lipase activity of the dispersed pancreatin prior to heating.

15. The process of claim 14 wherein the lipase activity of the dispersed pancreatin after heating is at least about 90% of the lipase activity of the dispersed pancreatin prior to heating.

16. A process for the manufacture of pancreatin, comprising the steps of:
heating a dispersed form of pancreatin having a total solvent content equal to or less than 1% at:
(a) a temperature from 80° C. to 90° C. for a period of between about 30 hours and about 48 hours,
(b) a temperature from 85° C. to 95° C. for a period of between about 12 hours and about 30 hours, or
(c) a temperature from 95° C. to 100° C. for a period of between about 6 hours and about 12 hours;
wherein the titer level of any porcine parvovirus present in the dispersed pancreatin after heating is at least about 1000 times less than the titer level of said porcine parvovirus present in the dispersed pancreatin prior to heating; and
wherein lipase activity of the dispersed pancreatin after heating is at least about 70% of lipase activity of the dispersed pancreatin prior to heating.

17. The process of claim 16 wherein the lipase activity of the dispersed pancreatin after heating is at least about 90% of the lipase activity of the dispersed pancreatin prior to heating.

18. The process of claim 16 wherein the heating step is performed continuously.

19. The process of claim 16 wherein the heating step is performed discontinuously.

20. The process of claim 16 wherein the heating of the pancreatin is at a temperature from 80° C. to 90° C. for a period of between about 30 hours and about 48 hours.

21. The process of claim 16 wherein the heating of the pancreatin is at a temperature from 85° C. to 95° C. for a period of between about 12 hours and about 30 hours.

22. The process of claim 16 wherein the heating of the pancreatin is at a temperature from 95° C. to 100° C. for a period of between about 6 hours and about 12 hours.

* * * * *